United States Patent [19]
Hossack

[11] Patent Number: 5,735,282
[45] Date of Patent: *Apr. 7, 1998

[54] FLEXIBLE ULTRASONIC TRANSDUCERS AND RELATED SYSTEMS

[75] Inventor: John A. Hossack, Palo Alto, Calif.

[73] Assignee: Acuson Corporation, Mountain View, Calif.

[*] Notice: The term of this patent shall not extend beyond the expiration date of Pat. No. 5,680,863.

[21] Appl. No.: 716,517

[22] Filed: Sep. 18, 1996

Related U.S. Application Data

[63] Continuation-in-part of Ser. No. 657,646, May 30, 1996.

[51] Int. Cl.$^6$ ........................................................ A61B 8/00
[52] U.S. Cl. .............................. 128/662.03; 128/662.06
[58] Field of Search ........................ 128/662.03, 662.06; 310/327, 328, 334

[56] References Cited

U.S. PATENT DOCUMENTS

| | | |
|---|---|---|
| 4,468,747 | 8/1984 | Leavitt et al. . |
| 4,471,449 | 9/1984 | Leavitt et al. . |
| 4,734,963 | 4/1988 | Ishiyama . |
| 4,989,143 | 1/1991 | O'Donnell et al. . |
| 5,044,053 | 9/1991 | Kopel et al. . |
| 5,148,810 | 9/1992 | Maslak et al. . |
| 5,297,553 | 3/1994 | Sliwa, Jr. et al. . |
| 5,335,663 | 8/1994 | Oakley et al. . |
| 5,363,852 | 11/1994 | Sharkawy ............................. 128/662.03 |
| 5,423,771 | 6/1995 | Imran . |
| 5,465,724 | 11/1995 | Sliwa, Jr. et al. . |
| 5,479,930 | 1/1996 | Gruner et al. . |

FOREIGN PATENT DOCUMENTS

WO 94/13411   6/1994   WIPO .

OTHER PUBLICATIONS

"Adaptive Ultrasound Imaging Systems Using Large, Two–Dimensional, Conformal Arrays"; Pai–Chi Li, et al.; 1994 Ultrasonics Symposium; pp. 1625–1628.

"Phase Aberration Correction on Two–Dimensional Conformal Arrays"; Pai–Chi Li and Matthew O'Donnell; IEEE Transactions on Ultrasonics, Ferroelectrics, and Frequency Control, vol. 42, No. 1, Jan. 1995; pp. 73–82.

"A Flexible Ultrasonic Array Incorporating a Platelet Composite Transmitter—Theory and Experiment"; D.J. Powell and G. Hayward; 1993 Ultrasonics Symposium; pp. 687–690.

"A Novel Ultrasonic Array Incorporating Composite Transducer Technology"; D.J. Powell and G. Hayward; 1992 Ultrasonic Symposium; pp. 527–530.

"A Performance Appraisal of Flexible Array Structures Using A Facet Ensemble Scattering Technique"; D.J. Powell and G. Hayward, Ultrasonics Research Group; 1991 Ultrasonic Symposium; pp. 753–756.

"Flexible Ultrasonic Transducer Arrays for Nondestructive Evaluation Applications—Part I: The Theoretical Modeling Approach"; David J. Powell and Gordon Hayward; IEEE Transactions on Ultrasonics, Ferroelectrics, and Frequency Control, vol. 43, No. 3, May 1996; pp. 385–392.

(List continued on next page.)

*Primary Examiner*—Marvin M. Lateef
*Assistant Examiner*—Derrick Fields
*Attorney, Agent, or Firm*—Brinks Hofer Gilson & Lione

[57] ABSTRACT

An ultrasonic imaging system includes an ultrasonic transducer having multiple ultrasonic transducer elements which are movable between at least first and second configurations which differ in curvature. The transducer elements supply receive signals to a receive beamformer, and the receive beamformer supplies output signals to a scan converter, which is controlled by a scan converter controller. The scan converter controller generates a control signal indicative of the configuration of the transducer elements, and the scan converter responds to this control signal to reduce image distortion associated with movement of the transducer elements between the first and second configurations.

14 Claims, 18 Drawing Sheets

OTHER PUBLICATIONS

"Flexible Ultrasonic Transducer Arrays for Nondestructive Evaluation Applications—Part II: Performance Assessment of Different Array Configurations"; David J. Powell and Gordon Hayward; IEEE Transactions on Ultrasonics, Ferroelectrics, and Frequency Control, vol. 43, No. 3, May 1996; pp. 393–402.

"Phase Aberration Correction In Two Dimensions Using A Deformable Array Transducer"; Loriann L. Ries and Stephen W. Smith; 1995 IEEE Ultrasonics Symposium.

"Medical Ultrasonic Probe Using PZT/Polymer Composite"; Hiroshi Takeuchi, et al.; 1984 Ultrasonics Symposium; pp. 507–510.

"Shape Calibration For A Nominally Linear Equispaced Array"; Jean–Jacques Fuchs; 1993 IEEE; pp. IV–300–IV–303.

"A Scan Conversion Algorithm For Displaying Ultrasound Images"; Steven C. Leavitt, et al.; Hewlett–Packard Journal Oct. 1983; pp. 30–34.

"Laparoscopic Transducer Type 8555"; B&K Medical.

"Laparoscopic and Thoracoscopic Surgery"; Constantine T. Frantzides, MD, PhD, FACs; Mosby; pp. 187–195.

"Fundamentals of Laparoscopic Surgery", Lawrence W. Way, M.D., et al.; Churchill Livingstone; pp. 67–38.

"Principles of Laproscopic Surgery Basic and Advanced Techniques, Laparoscopic Ultrasound: Principles and Techniques"; Daniel Castro, et al.; pp. 489–505.

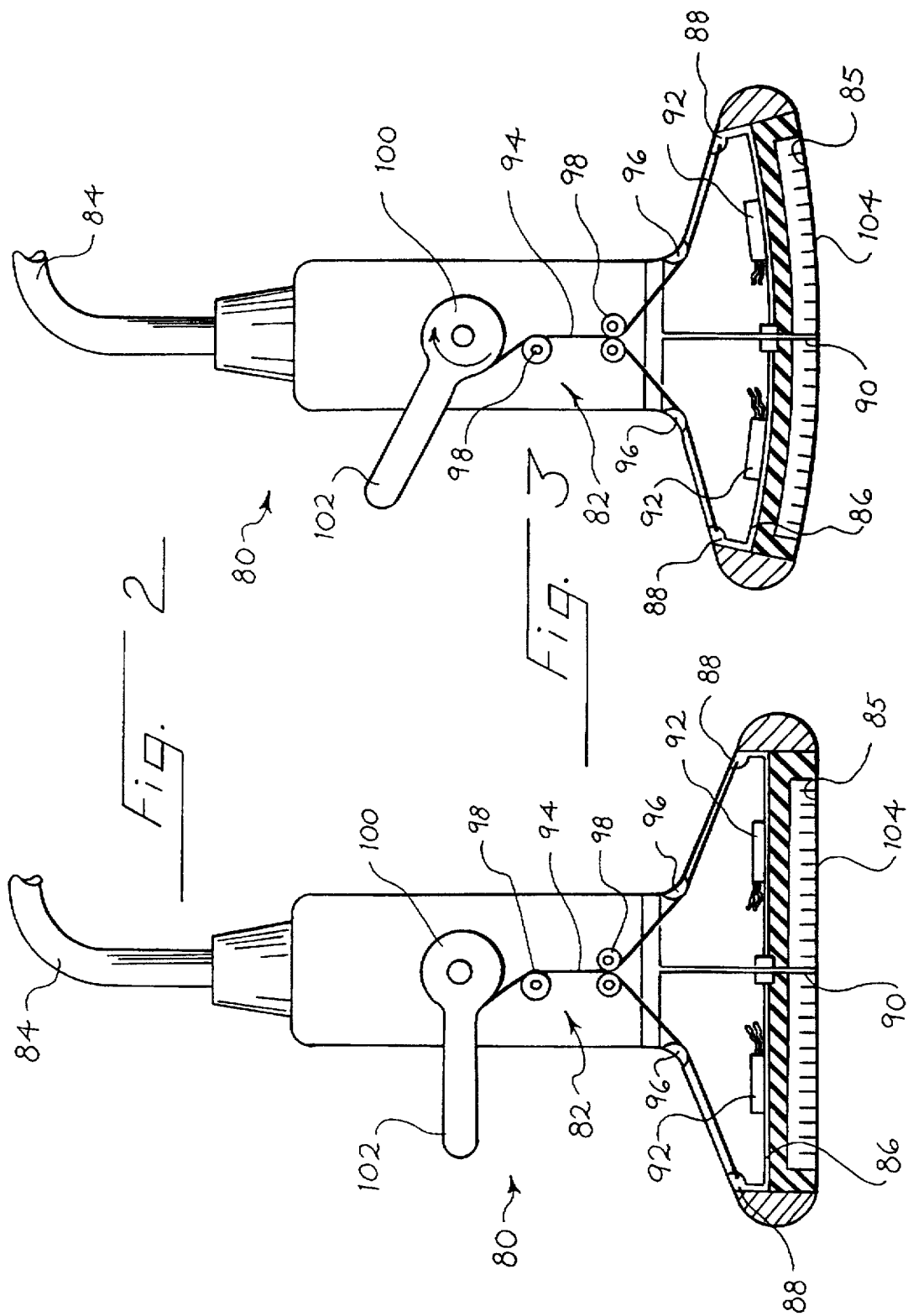

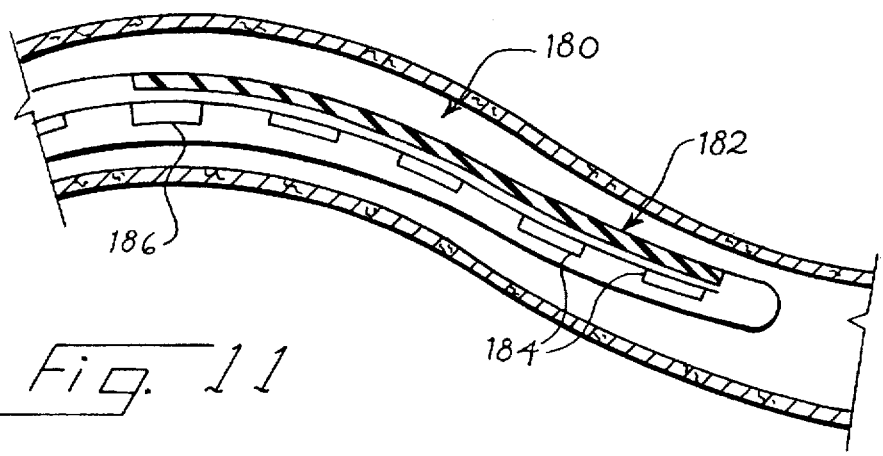
Fig. 11
Fig. 12
Fig. 13
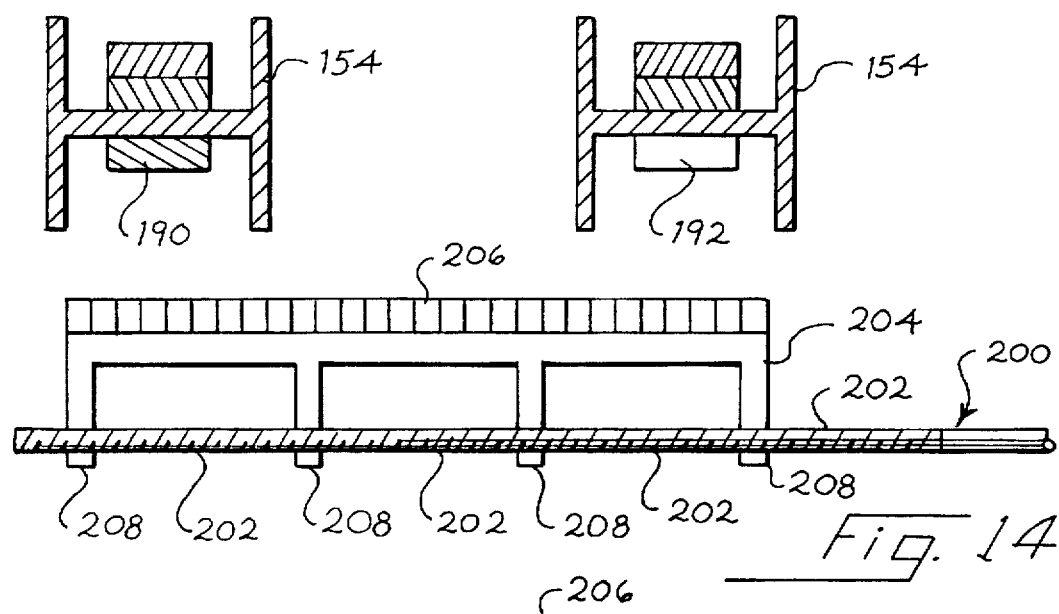
Fig. 14
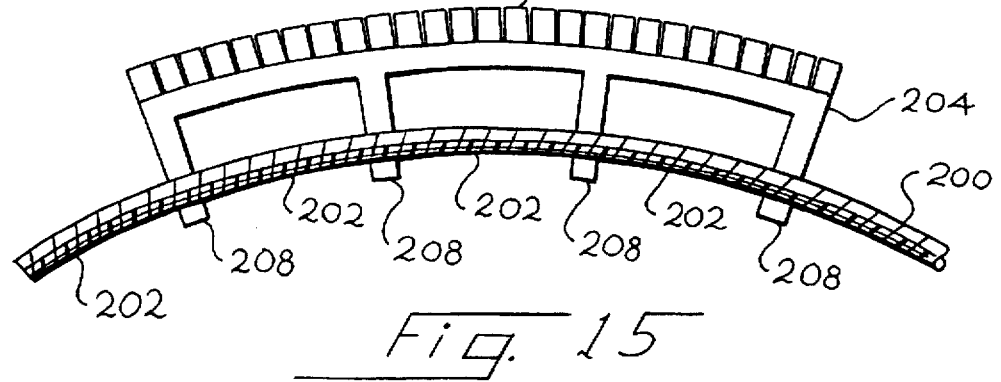
Fig. 15

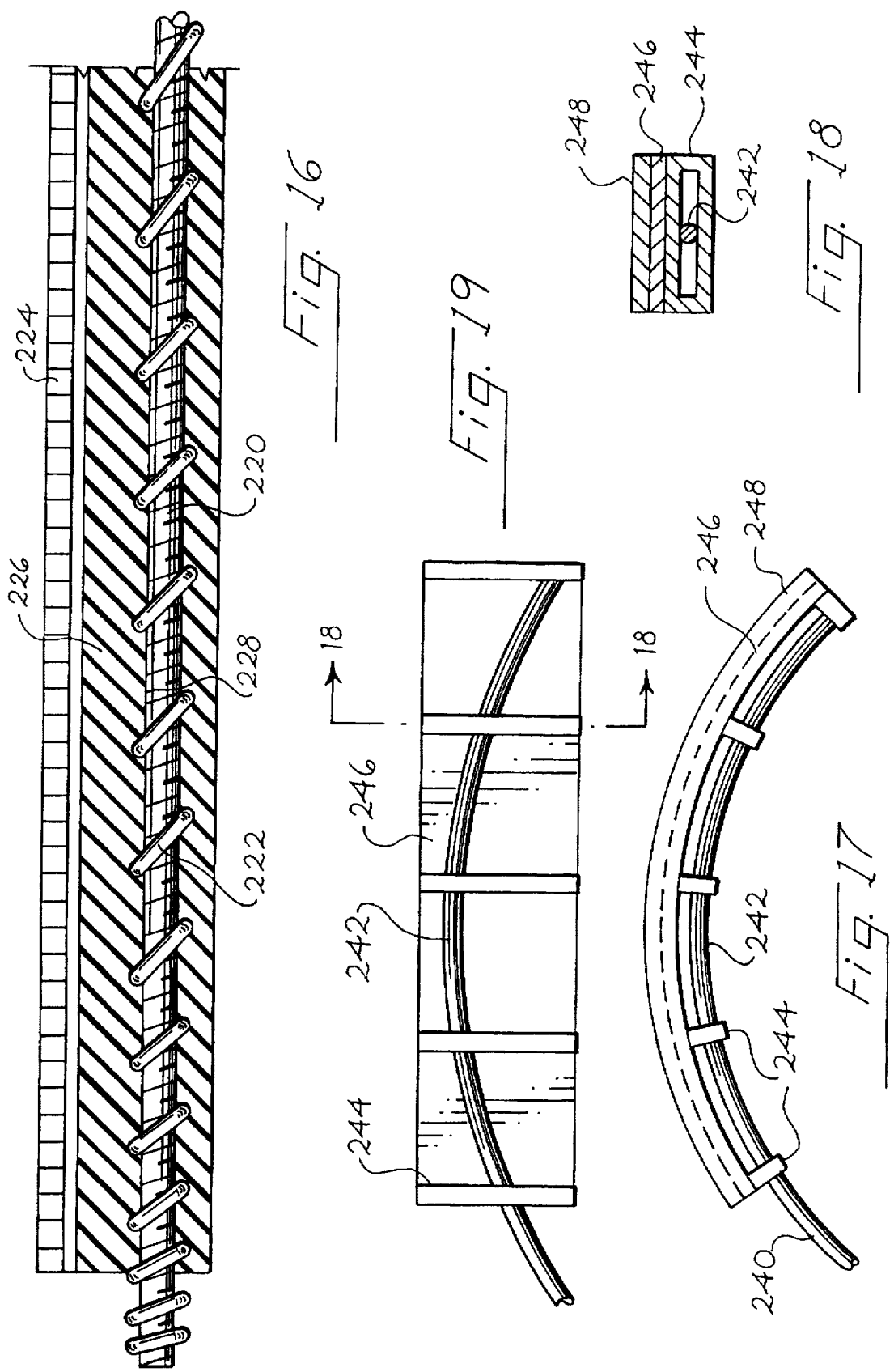

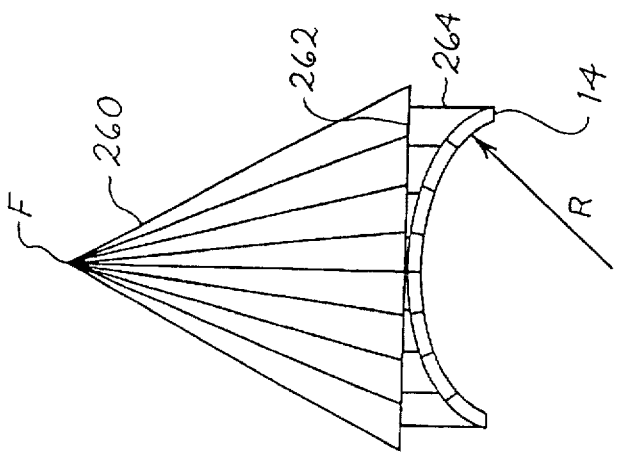
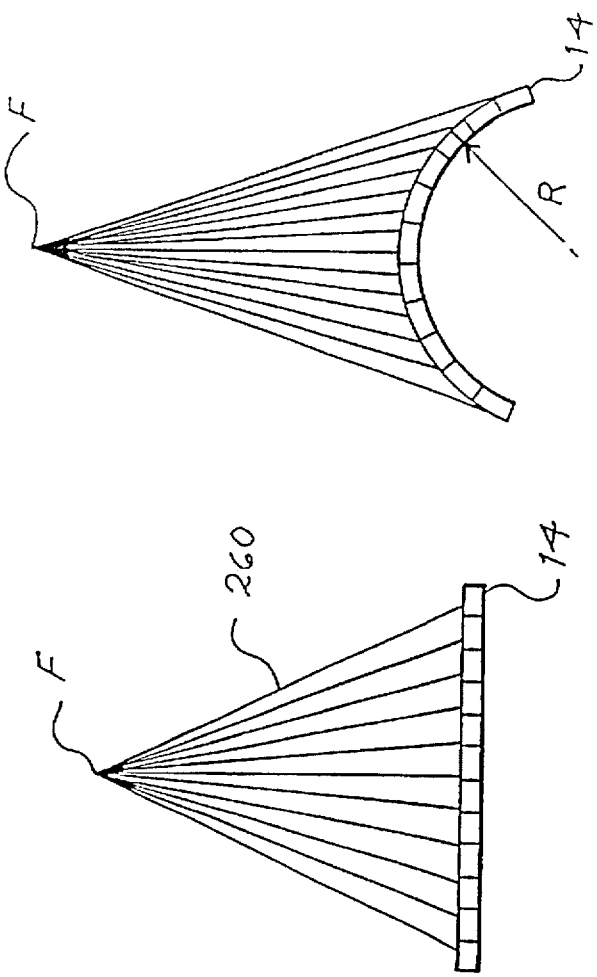

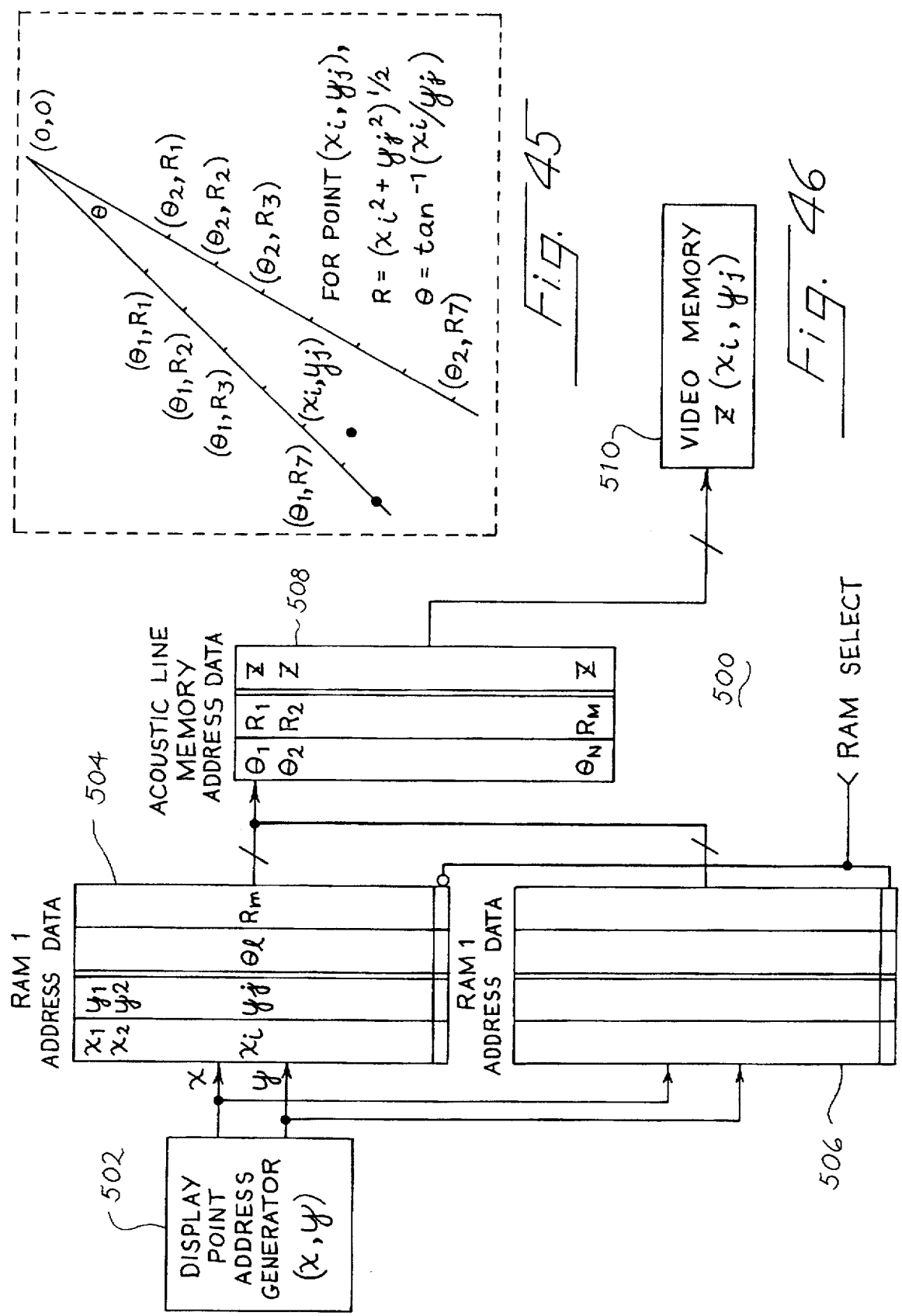

FLEXIBLE ULTRASONIC TRANSDUCERS AND RELATED SYSTEMS

CROSS REFERENCE TO RELATED APPLICATION

This is a continuation-in-part of copending U.S. patent application Ser. No. 08/657,646 filed May 30, 1996.

BACKGROUND OF THE INVENTION

This invention relates to the field of ultrasonic imaging transducers and to systems for operating such transducers.

Ultrasonic imaging systems have in the past used a wide variety of transducer arrays, including both planar arrays and convexly curved arrays. On occasion steering capabilities have been provided, as for example with array rotating systems such as those shown in Sliwa U.S. Pat. No. 5,465,724, assigned to the assignee of the present invention.

Conformable medical arrays have been disclosed which are designed to conform to the body wall, as described by P. Li, et al. in the following papers: "Adaptive Ultrasound Imaging Systems Using Large, Two-Dimensional, Conformal Arrays" (1994 Ultrasonics Symposium, IEEE, pp. 1621-1628); and "Phase Aberration Correction on Two-Dimensional Conformal Arrays" (IEEE Transactions on Ultrasonics, Ferroelectrics and Freq. Cont., 42, 1, pp. 73-82 (1995)). Correlation based phase correction is used to compensate for focusing errors. Flexible arrays have also been used for non-destructive engineering testing, as described by D. J. Powell and G. Hayward in the following papers: "A Flexible Ultrasonic Array Incorporating a Platelet Composite Transmitter—Theory and Experiment" (1993 Ultrasonics Symposium, IEEE, pp. 687-690); "A Novel Ultrasonic Array Incorporating Composite Transducer Technology" (1992 Ultrasonics Symposium, IEEE, pp. 527-529); and "A Performance Appraisal of Flexible Array Structures Using a Facet Ensemble Scattering Technique" (1991 Ultrasonics Symposium, IEEE, pp. 753-756). These arrays are applied to pipe like structures, and take on the curvature of the structure.

1.5 D arrays are known with deformable sections, as described by L. Ries and S. Smith in the paper entitled "Phase Aberration Correction in Two Dimensions Using a Deformable Array Transducer" (IEEE, 1995 Ultrasonics Symposium). In this case small motions in the off-center elements are made using actuators in order to control elevational focusing.

The present invention is directed to new transducer arrays which provide new capabilities to the operator.

SUMMARY OF THE INVENTION

According to this invention, an ultrasonic imaging system comprises a receive beamformer and an ultrasonic transducer comprising a plurality of ultrasonic transducer elements. The transducer elements are movable between at least first and second configurations which differ in curvature, and the transducer elements supply receive signals to the receive beamformer. A scan converter controller generates a control signal indicative of configuration of the transducer elements, and a scan converter, responsive to the receive beamformer and to the control signal, reduces image distortion associated with movement of the transducer elements between the first and second configurations. In alternative embodiments, the scan converter controller may be responsive to a shape transducer signal indicative of the configuration of the transducer elements, or an actuator coupled to the transducer elements to move the transducer elements between the first and second configurations. Alternately, the scan converter controller may include a correlator responsive to the receive signals to estimate configuration of the transducer elements based on the receive signals. This correlator may include a cross-correlator or other time of flight estimator.

Further features and advantages of the present invention will be described below in conjunction with the detailed description.

BRIEF DESCRIPTION OF THE DRAWINGS

FIGS. 2 and 3 are two side views in partial section of the transducer of FIG. 1.

FIG. 11 is a view of a yet another transducer suitable for use in the system of FIG. 1.

FIGS. 12 and 13 are schematic cross-sectional views of alternative transducers which are in certain respects similar to that of FIG. 8.

FIGS. 14 and 15 are side views of a flexible transducer which is actuated by a threaded rod, in two alternative curvature configurations.

FIG. 16 is a fragmentary sectional view of another transducer suitable for use in the system of FIG. 1.

FIG. 17 is a side view of another flexible transducer suitable for use in the system of FIG. 1.

FIG. 18 is a cross-sectional view of the transducer of FIG. 17, taken along lines 18—18 of FIG. 19.

FIG. 19 is a bottom view of the transducer of FIG. 18.

FIGS. 20, 21, and 22 are schematic views that illustrate various approaches to determining focusing delays for a flexible transducer.

FIGS. 27 and 28 are views of indicia that may be displayed to show the curvature of the array.

FIG. 45 is a schematic view of two acoustic lines, showing a θ, R addressing scheme.

FIG. 46 is a schematic view of a scan converter suitable for use with this invention.

DETAILED DESCRIPTION OF THE PRESENTLY PREFERRED EMBODIMENTS

Figure 1:
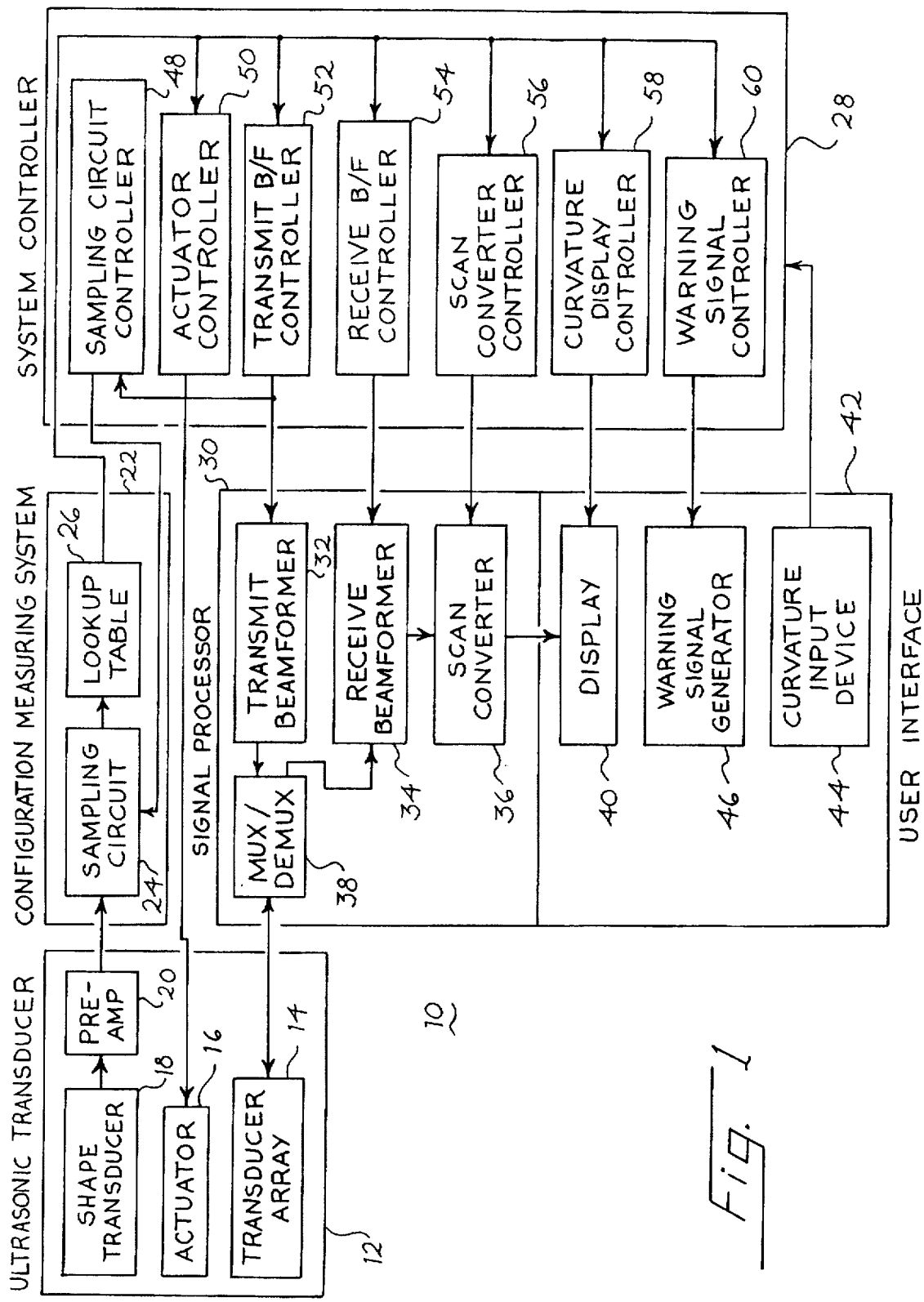
FIG. 1 is a block diagram of an ultrasonic imaging system that incorporates a presently preferred embodiment of this invention.

Turning now to the drawings, FIG. 1 is a block diagram of a medical ultrasonic imaging device that incorporates presently preferred embodiments of the present invention. The block diagram of FIG. 1 is a high level block diagram and the following detailed discussion will discuss several of these blocks in greater detail.

As shown in FIG. 1, an ultrasonic imaging system 10 includes an ultrasonic transducer 12 which includes a transducer array 14. The array 14 includes multiple ultrasonic transducers arranged along at least one axis. In alternative embodiments the array 14 can be a two dimensional array or a 1.5 dimensional array of ultrasonic transducers. The ultrasonic transducer 12 also includes one or more actuators 16. The actuator 16 can take many forms, as described below, but in each case the basic function of the actuator 16 is to control the curvature or configuration of the transducer array 14. As explained below, the actuator 16 in some embodiments can move the transducer array 14 into one of two distinct configurations, each characterized by pre-selected curvature about an axis extending along one dimension of the transducer array. In other embodiments the actuator 16 is used to vary the curvature of the transducer array 14 within a continuous range of curvatures.

As shown in FIG. 1, the ultrasonic transducer 12 also includes in this embodiment one or more shape transducers 18. These shape transducers can take many forms, but in each case they provide an output signal that is indicative of the instantaneously prevailing curvature of the transducer array 14. In some cases the shape transducers 18 take the form of strain gauges coupled to the transducer array 14. In many cases it will be preferable to include a preamplifier 20 adjacent to the transducer array 14 in order to amplify the output signal of the shape transducer 18 before this signal is transmitted over any substantial distance.

As shown in FIG. 1, the system 10 includes a transducer configuration measuring system 22. The system 22 includes a sampling circuit 24 and a lookup table 26. The sampling circuit 24 is responsive to the output signal of the shape transducer 18 to sample the signal at selected times and to supply the sampled signal to the lookup table 26. The lookup table 26 can be a read only memory that performs a conversion, for example between the units of measurement supplied by the sampling circuit 24 and a standard unit of measurement such as radius of curvature at the active surface of the array 14 expressed in millimeters. The output signal of the lookup table 26 is applied to a system controller 28. In this way, the system controller 28 is provided with real time information regarding the instantaneously prevailing curvature of the transducer array 14.

The transducer array 14 is connected to a signal processor 30 which includes a transmit beamformer 32, a receive beamformer 34, and a scan converter 36. The transmit beamformer 32 and the receive beamformer 34 are connected to respective transducers included in the transducer array 14 by a multiplexer/demultiplexer 38. During excitation in any conventional mode (including for example, in B-mode, color Doppler velocity, Doppler energy) the transmit beamformer 32 supplies high voltage pulses via the multiplexer/demultiplexer 38 to the transducer array 14. These pulses are timed and phased to operate the transducer array 14 as a phased array, thereby focusing ultrasonic energy along a desired scan line proceeding outwardly from the transducer array 14. After the completion of an excitation event, the transducers of the array 14 receive reflected ultrasonic energy from tissue being examined and generate signals in response to this reflected energy. These signals are transmitted by the multiplexer/demultiplexer 38 to the receive beamformer 34. The receive beamformer 34 applies desired time delays and phase adjustments to cause these signals from the transducers of the array 14 to add coherently at selected focal points arranged along receive scan lines. This coherently summed image information is provided to the scan converter 36, which generates image signals suitable for display on a display 40.

The display 40 is included in a user interface 42, and this user interface 42 additionally includes a curvature input device 44. As explained below, the device 44 can be used to generate a curvature signal that is supplied to the system controller 28. This signal is indicative of a desired curvature for the transducer array 14. The interface 42 also includes a warning signal generator 46 that is controlled by the system controller 28.

The system controller 28 includes in this example seven separate controllers, each associated with a respective subsystem. The sampling circuit controller 48 controls the sampling circuit 24 to cause sampling of the output signal of the shape transducer 18 during times between ultrasonic pulses generated by the transducer array 14. In alternative embodiments this function can be performed either by causing the sampling circuit controller 48 to initiate operation of the sampling circuit 24 or to inhibit operation of the sampling circuit 24 during respective appropriate periods.

The actuator controller 50 responds to the output signal of the curvature input device 44 to control the actuator 16 as appropriate. Preferably, the actuator controller 50 is responsive both to the output signal of the lookup table 26 and to the output signal of the curvature input device 44 to provide closed loop operation. This allows a user to select a desired curvature for the transducer array 14, and then to rely on the actuator controller 50 to achieve the desired curvature automatically.

The transmit beamformer controller 52 also responds to the output signal of the lookup table 26 to control the transmit beamformer 32 appropriately. As described in greater detail below, the transmit beamformer controller 52 provides information to the transmit beamformer 32 that identifies the power level adjustment and the delay values appropriate for the instantaneously prevailing curvature of the transducer array 14.

The receive beamformer controller 54 supplies similar control information to the receive beamformer 34 to allow the receive beamformer 34 to use apodization values and delay values appropriate for the instantaneously prevailing curvature of the transducer array 14. Similarly, the scan converter controller 56 supplies control information to the scan converter 36 that defines the location of the scan lines formed by the receive beamformer 34. The scan converter 36 responds to this information appropriately to convert image information from the frame of reference of the scan lines of the receive beamformer 34 to the frame of reference appropriate for the display 40.

The curvature display controller 58 provides display information to the display 40 that causes the display 40 to display indicia indicative of the instantaneously prevailing curvature of the transducer array 14. These indicia allow a user to determine quickly the configuration of the array 14 at any point in time. These indicia may take the form of pictograms showing the curvature of the array 14, numerals that communicate the current radius of curvature of the array 14, and/or legends that identify the current configuration of the array 14 (e.g., planar, convex). FIGS. 27 and 28 show indicia that may be used to indicate a straight array and a curved array, respectively. As the numerical indication of radius approaches a lower limit, it can be caused to flash or displayed in reverse video. When the entire beamformed image is displayed, the shape of the top of the image illustrates the curvature of the array.

The warning signal controller 60 controls the warning signal generator 46 to sound an alarm when curvature limits of the transducer array 14 are met or exceeded.

The following sections provide additional details regarding a range of alternatives suitable for use as components of the imaging system 10.

Transducer

The transducer 12 described above can take many forms, including the following. It should be noted that not all forms of the transducer include actuators, and similarly not all forms include shape transducers.

Flexible linear array in a T-shaped package

FIG. 2 shows a transducer 80 intended for use outside the body. The transducer 80 includes a handle 82 which supports at one end a cable 84. The cable 84 carries all signals required for the signal processor 30, the transducer configuration measuring system 22, and the system controller 28 of FIG. 1. The opposite end of the handle 82 supports a transducer array 85, which in this embodiment includes a linear array of piezoelectric transducer elements. The transducer array 85 is mounted on a flexible support element 86 which terminates at each end at a respective anchor 88. A center support 90 is secured to a central portion of the support element 86 and to the handle 82 to maintain the array 85 in a centered relationship with respect to the handle 82. One or more strain gauges 92 are mounted on the side of the support element 86 opposite the array 85. The strain gauges are oriented to detect curvature of the support element 86 in the plane of FIG. 1.

Cables 94 are fixedly connected to the anchors 88, and these cables 94 pass via guides 96 and pulleys 98 to a control pulley 100. The control pulley 100 includes a handle 102 which can be controlled by a user. FIG. 2 shows the control pulley 100 in a first position, in which the transducer array 85 is substantially planar. FIG. 3 shows the control pulley 100 in a rotated position, in which the control pulley 100 has applied tension to the cables 94 to flex the support element 86 and the array 85 to a second configuration, in which the array 85 is convexly curved. The strain gauges 92 detect the curvature of the support element 86, which is related in a one-to-one fashion with the curvature of the array 85. The control pulley 100 and the handle 102 operate as an actuator, which in this case is under the direct manual control of the user, rather than under the control of the system controller. The resilience of the support element 86 returns the array 85 to the configuration of FIG. 2 when the handle 102 is returned to the position of FIG. 2.

The transducer array 85 and the support element 86 are covered by a flexible outer layer 104. The transducer array 85 is connected to the individual conductors of the cable 84 by a flex circuitry (not shown). By way of example, the support element 86 can be a steel shim. In some applications the backing block of the transducer array 85 may itself form the support element. When the support element 86 is bent as shown in FIG. 3, the stress is greatest near the center of the support element 86 because of the leverage effect, i.e., the point of application of force is farther from the center than from the ends of the support element 86. This leverage effect can result in the curvature of the array 85 being tightest in the center. If this a problem, the support element 86 can be made stiffer (for example, thicker) in the middle to compensate.

The outer layer 104 can be formed of a room temperature vulcanizing rubber cast around the articulating parts with a balloon-type arrangement creating an air space for the moving parts to move in. Alternately, a polyurethane tube can be placed over the flexible portion of the transducer 80. Such polyurethane tubes are currently used on the flexible sections of certain transducers. Other suitable materials may include other soft plastic tubes.

The cables 94 act as tension members, and it will be understood that a wide variety of materials and structures can be used for such tension numbers.

A user can operate the handle 102 and control pulley 100 to select the scan format produced by the transducer 80. In particular, the convex configuration of the FIG. 3 provides scan lines that diverge from one another so as to substantially expand the field of view of the array 85 when positioned as shown in FIG. 3 as compared as to the configuration shown in FIG. 2.

Laparoscopic Transducer

Figure 4:
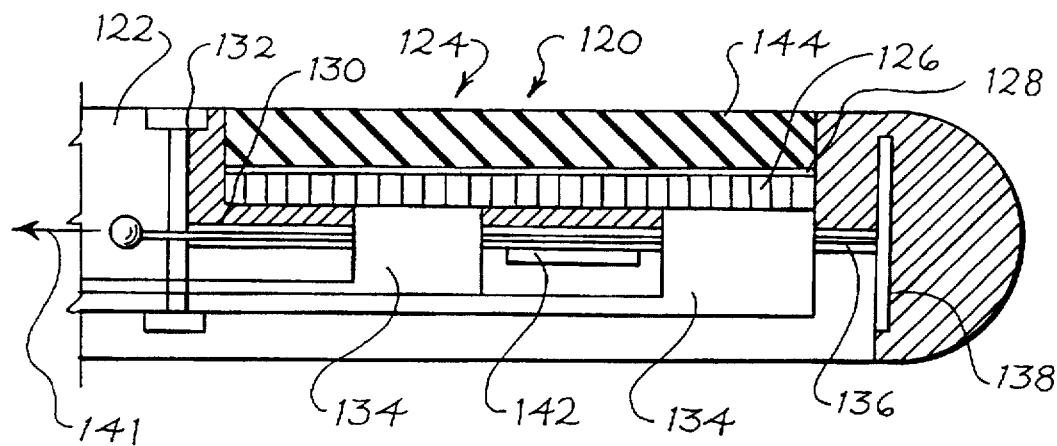
FIG. 4 is a longitudinal sectional view of a portion of an alternative transducer for use in the system of FIG. 1.
Figure 5:
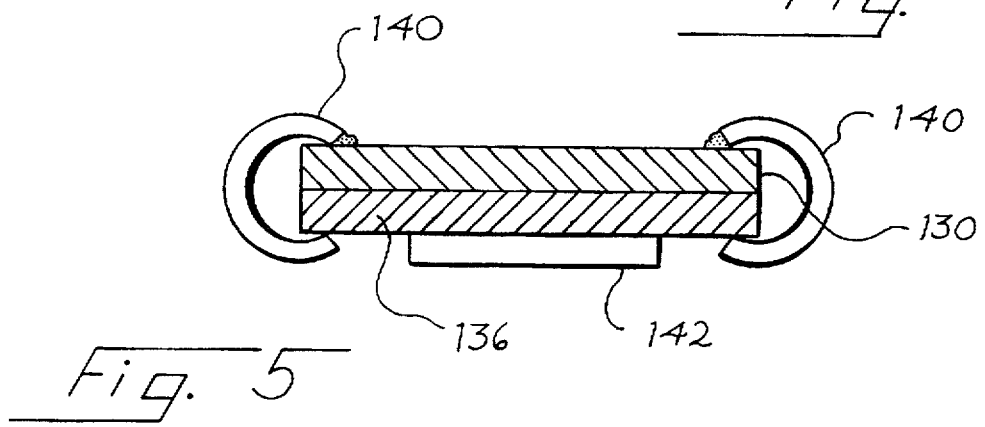
FIG. 5 is a cross-sectional view showing a portion of the transducer of FIG. 4.
Figure 6:
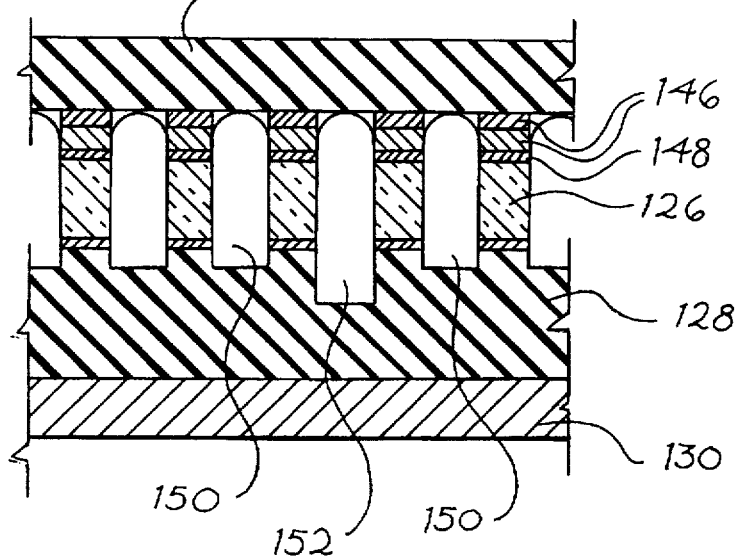
FIG. 6 is an enlarged cross-sectional view of a portion of the transducer array included in the transducer of FIG. 4.

Turning now to FIGS. 4–6, these figures show various views of a laparoscopic transducer 120 intended for installation at one end 122 of a laparoscope. The transducer 120 forms the extreme distal end 124 of the laparoscope, which will typically include a conventional articulated section adjacent to the transducer 120.

As best shown in FIG. 4 the transducer 120 includes a linear array of piezoelectric transducer elements (PZT elements) 126. These PZT elements 126 are mounted on a thin, flexible backing block 128, which is in turn mounted to an upper plate 130. The upper plate 130 is secured to a proximal anchor plate 132 that is secured in place to the body 122 of the laparoscope. Flex circuits 134 extend from the PZT elements 126 to the body 122 of the laparoscope. A lower plate 136 is mounted alongside and beneath the upper plate 130. This lower plate 136 supports a distal anchor plate 138. As shown in FIG. 5, a plurality of loops 140 are rigidly secured to one of the plates 130, 136 while sliding against the surface of the other of the plates 130, 136. These loops 140 are spaced along the length of the plates 130, 136 to constrain the plates 130, 136 to bend together, while allowing sliding motion therebetween. One or more strain gauges 142 are mounted to the lower plate 136. A tension member such a cable 141 is mounted to the lower plate 136 to pull the lower plate 136 with respect to the upper plate 130 (FIG. 4).

The following construction details clarify one possible construction of the elements associated with the PZT elements 126. The backing block 128 in this embodiment is approximately 1.2 millimeters thick and is formed of a high loss, flexible material. One such material includes polymeric particles which are fused to form a macroscopically rigid structure having remnant tortuous permeability, as described in U.S. Pat. No. 5,297,553, assigned to the assignee of this invention. Another material for the backing block 128 is that sold under the trade name Plastiform 2004D flexible magnet material, available from Arnold Engineering Company of Norfolk, Nebr. and 3M. Other materials comprising combinations of epoxies, glass microballoons, metallic particles and plasticizers may be used.

Figure 7:
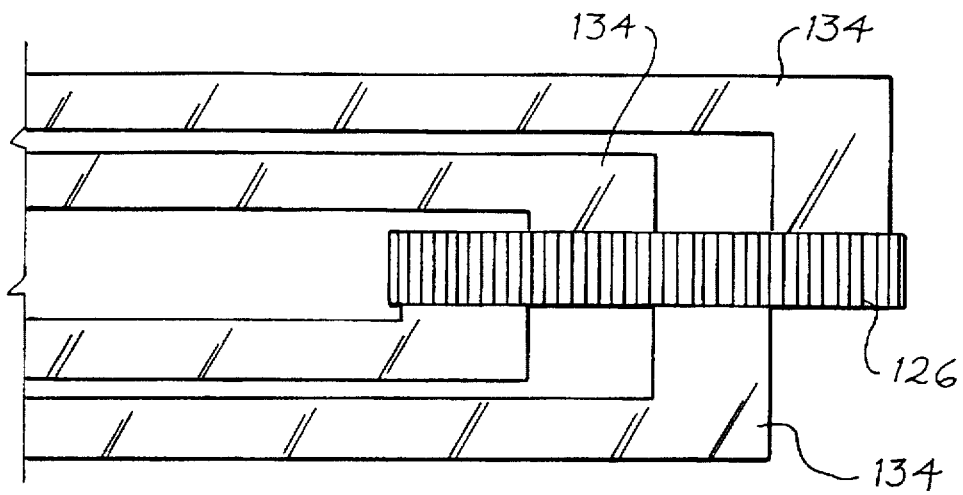
FIG. 7 is a plan view of portions of the transducer array and flex circuit segments of the transducer of FIG. 4, prior to final assembly.

The flex circuits 134 are conventional in the field, and can be obtained, for example, from Sheldahl of Northfield, Minn. Since the flex circuit must flex along the azimuth and simultaneously fold around the back of the array in this embodiment, it is preferred to use multiple flex circuit segments. In an array of 128 PZT elements 126, each on a 0.3 millimeter pitch, it may be advisable to have eight or more individual flex segments. The more flex segments that are used, the greater the ability of the array 126 to flex. However, when multiple layers of flex circuit are folded on top of one another, there can be a disadvantage associated with the increased overall thickness of the assembly and the increased vulnerability to cross talk. FIG. 7 shows one arrangement of flex curvature 134, before they are folded under the array 126.

The PZT elements of the array 126 are preferably formed of the material sold by Motorola as material 3203HD. Alternative PZT ceramics may be used. Typically, the PZT elements are lapped and electroded with sputtered high purity gold over a suitable adhesion layer such as nickel or chromium.

As shown in FIG. 6, the upper surface of the PZT elements supports a copper foil 148 which acts as a ground return. This foil can be, for example, 0.0008 inches in thickness. Often, one or more matching layers 146 are used. The layer adjacent the copper foil 148 can be a high impedance layer, for example a ceramic such as alumina or lithium aluminum silicate and/or a metal powder such as tungsten (325 mesh) loaded epoxy with an impedance of approximately 8–10 MRayls. The lower impedance matching layer 146 can be an unloaded polymer such as epoxy, with an impedance of approximately 2.5 MRayls.

These elements of the transducer 120 can be manufactured by laminating the PZT elements, the copper foil 148 and the matching layers 146 together using a low viscosity epoxy such as Hysol RE2039-HD3561 supplied by Hysol, of industry, Calif., in a suitably designed press as well known in the art. After the epoxy has cured, the laminated surface is placed in a semiconductor wafer slicing saw. Periodic cuts are made from the top down to the backing block 128 to a depth of approximately 10 mils. These cuts create kerfs 150, 152 aligned with the traces of the flex circuits 134.

Preferably the kerfs 150, 152 between the PZT elements 126 are not filled. If they were the array would lose a considerable degree of flexibility. For this reason the preferred lens structure is formed from a molded silicone material, such as that supplied by Dow Corning as material RTV577 (Midland, Mich.). This lens 144 may then be adhered to the diced upper surface of the transducer array. The curvature of the upper surface of the lens 144 is selected to give a desired elevational focal depth. The lens 144 is as thin as possible consistent with electrical safety and reliability concerns, as for example, 0.5 millimeters in thickness. A silicone such as RTV577 can be used as the adhesive. If a small amount of the adhesive penetrates into the kerfs 150, 152, an interlocked bond will be formed.

The upper plate 130 is formed from a spring steel and is approximately 5 to 10 mils in thickness (FIG. 5). The lower plate 136 can be formed of a similar material. The loops 140 maintain the upper and lower plates 130, 136 in close proximity to one another at all radii of curvature.

Note that the kerfs 150, 152 can be of differing depths. For example, the deeper kerfs 152 can be placed intermittently, with one or more shallower kerfs 150 interposed within the deeper kerfs 152. When this arrangement is used the transducer array will bend preferentially at the deeper kerfs 152, with straighter sections therebetween. This arrangement can be used to ensure that most of the curvature occurs between flex circuit segments rather than within them.

The natural resilience of the upper and lower plates, 130, 136 biases the transducer array to the position shown in FIG. 4. When a user desires to change the scan format, he can do so by applying tension to the cable 141. This can be done either manually with a user-controlled pulley of the type shown in FIG. 2, or electronically with a motor-driven tensioning device controlled by the system controller 28. Tension on the cable 141 displaces the lower plate 136 to the left with respect to the upper plate 130 as shown in FIG. 4. This causes the transducer array comprising the PZT elements 126 to assume a convex curvature.

Figure 8:
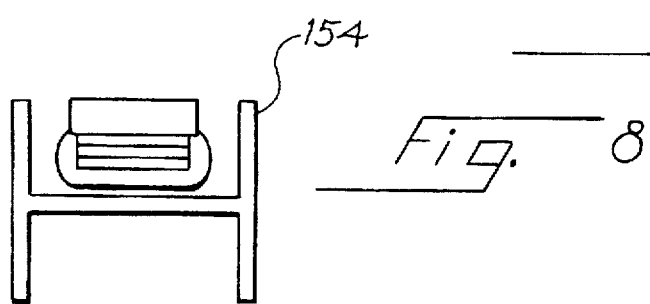
FIG. 8 is a schematic cross-sectional view of an alternative transducer which is similar in many respects to that of FIG. 4, and which is taken along line 8—8 of FIG. 9.
Figure 10:
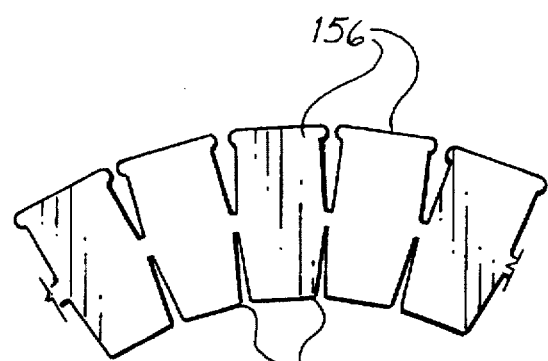
FIG. 10 is a side view corresponding to FIG. 9, showing the transducer in an alternative curvature configuration.
Figure 9:
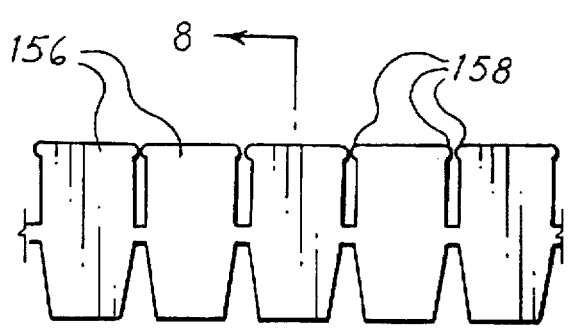
FIG. 9 is a fragmentary side view of the transducer FIG. 8.

FIGS. 8–10 relate to a curvature limiting device that can be used with the transducer 120. This curvature limiting device includes an "H" shaped element 154 which supports an array of blocks 156 on each side. The individual blocks 156 are trapezoidal, and are shaped to provide two limits to the curvature of the array. At one limit of curvature the points 158 touch, preventing further increase in curvature in the concave direction. The other limit to curvature is provided by the points 160, which touch to limit the maximum convex curvature. Thus, the blocks 156 limit curvature by abutting against one another in the two opposed directions of curvature. The central element of the "H" shaped structure can act as the upper plate 130 of FIG. 4, or the entire assembly including the PZT elements, the backing block 128, and the upper and lower plates 130, 136 can be mounted on one side of the "H" shaped structure 154. In either case, the control wire that applies tension to curve the element 154 is preferably offset with respect to the neutral axis of the element 154. The "H" shaped element 154 can be made of a suitable plastic such as polycarbonate or acetal. The thin middle portion is thin enough to permit easy flexing to the desired limits. By varying the taper angle of the blocks on 56, the designer can specify the limits of curvature.

Returning to FIG. 4, the flex circuits 134 are folded around the back of the backing block 128 and placed alongside the lower plate 136. Typically, layers of foil at ground potential are placed between adjacent layers of flex circuit 134 to minimize crosstalk. Additionally, if required, thin layers of PTFE plastic strip may be used to minimize abrasion damage.

The assembly described above can now be fitted into a flexible housing. One approach is to wrap and seal the moving parts of the array to form an air-filled void around them. This assembly may be fitted into a mold and the remaining space filled with a cold-curing polymer with suitable low durometer characteristics. An RTV polymer such as Dow Corning RTV577 may be suitable. Alternately, the subassembly may be inserted into thin, medical grade, flexible plastic tube formed of materials such as PEBAX, PVC or polyurethane. Typically, the lens 144 should be wetted to the inner surface of the thin tube, and ideally the lens 144 is bonded to the tube with adhesive. Alternately, a window can be formed in the tube, and the lens 144 can be exposed. Since one objective is to maintain the flexibility of the array, the cross-section of the transducer 120 is as wide as required by the PZT elements 126 and consistent with standard laparoscopic surgery dimensions. For example, the outside diameter can be made equal to 9.8 millimeters. The thickness dimension of the transducer 120 should be as thin as possible. The transducer 120 is linked to the endoscope portion of the laparoscope, which can be standard except for the addition of added conductors to cause the flexing of the array and to carry low voltage signals back from the strain gauge bridge. Suitable wires for the cable 141, which are thin, strong and exhibit minimum stretch, are those identified under the trade name Posilign and supplied by Bergen Cable Technologies of Lodi, N.J.

Figure 29:
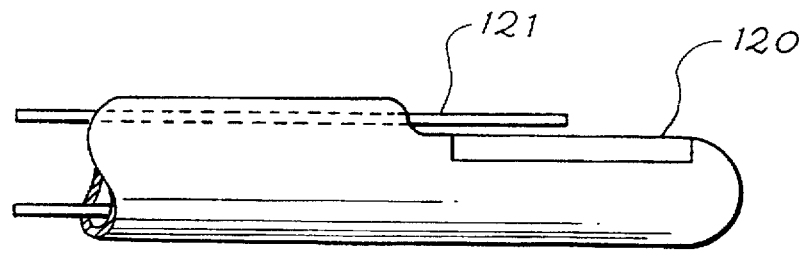
FIGS. 29 and 30 are two side views of a flexible transducer that is used in combination with a biopsy needle.
Figure 30:
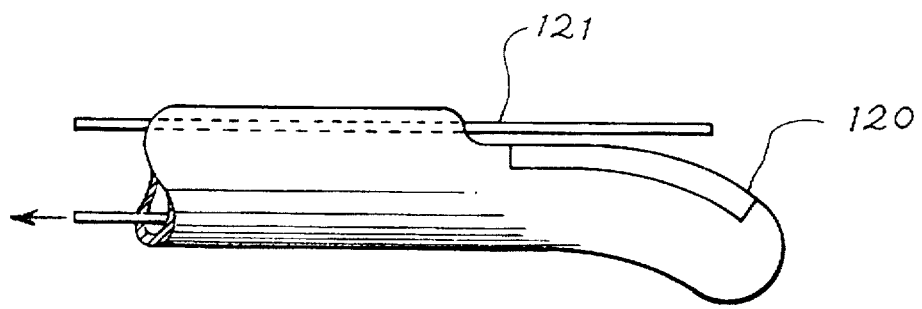

The transducer 120 described above may be used in combination with a surgical tool such as a biopsy needle, an electrocautery device, or a radio-frequency ablation device, for example. See Oakley U.S. Pat. No. 5,335,663 for a discussion of other types of transducers combined with a surgical tool. As shown in FIGS. 29–30, the transducer 120 is flexible and can be attached directly to a rigid tube-like support without an intermediate articulation section. A surgical tool such as a biopsy needle 121 is housed in a needle channel. The transducer 120 can be moved to the curved position of FIG. 30 to provide an improved field of view.

Intra-Luminal Array

FIG. 11 shows a cross-sectional view of a transducer array 180 suitable for use in intra-luminal applications. The transducer is sized to be inserted into blood vessels and similar lumens, and in this embodiment it is approximately 4 millimeters or less in diameter. The various elements of the array 182, including the PZT elements, flex circuit, and backing block (not shown), are configured to fit inside a medical-grade plastic tube having a small diameter, such as 4 millimeters. In this embodiment the backing block forms the support for the PZT elements, and there are no actuators. Immediately on the rear surface of the array 182 is placed a series of a miniature strain gauges 184. A gauge approximately 2 millimeters in width and 10 millimeters in length may be sufficient, and can be obtained from MicroMeasurements of Raleigh, N.C. Preferably, at least one preamplifier 186 is mounted on the transducer 180 immediately adjacent to the array 182. This preamplifier 186 amplifies the low voltage signals of the strain gauges 184 for transmission out of the body. One possibility is that the backing block for the array 182 be formed of the flexible magnetic material described above and that it be approximately 1 millimeter in thickness. Preferably there are multiple strain gauges 184 along the length of the array, so that S-shaped curvature can be detected and compensated for. Between the known radius values at the positions of the strain gauges 184 the local radius values at all other intermediate points can be determined by interpolation. Once the local radius at all points along the array 182 is known, local acoustic line origin and direction can be found by summing the incremental calculated vector displacements between elements.

The transducer 180 is designed to be flexible to follow the curvature of the vessel walls. The strain gauges 184 allow the system controller and the signal processor to obtain a useful image from the nonplanar array.

Actuators

The embodiments described above use cables to apply forces to flex the transducer arrays as desired. Of course, it should be understood that a wide variety of actuators can be used, either in combination with tension members as described above or in substitution for such tension members. For example, as shown in FIGS. 12 and 13 an actuator such as a shape memory metal element 190 or a bimetallic strip 192 can be affixed to the back of the support element 154. These actuators are particularly useful in combination with the curvature limiting blocks 156 shown in FIGS. 9–10.

Bimetallic actuators are commonly used in thermostatic applications and comprise laminated alloys having differing coefficients of thermal expansion. Bimetallic actuators are sold by a variety of companies including Demaich Industries, Johnson, and RI. Bimetallic actuators respond to variations in temperature. One method of heating the bimetallic actuator is to attach a resistive wire substrate to the bimetallic actuator, and to control the amount of current through it. Ambient temperature in the vicinity of the bimetallic actuator can be used to cool the strip and return it to its original shape. In the absence of external heating, the transducer array and the bimetallic actuator will reach an equilibrium temperature of about 37° C. when inserted into the body. In general, it is preferred to limit the maximum temperature to about 44° C. for safety reasons.

The shape memory metal actuator 190 of FIG. 13 can use a shape memory alloy such as Nitinol. This material has two phases: marstenitic and austenitic. The shape memory alloy is given one shape while it is hot. The alloy is cooled while maintaining the shape and then plastically deformed. Upon subsequent heating it will return to its original shape, prior to plastic deformation at the cold temperature. As with the bimetallic actuator, it is possible to heat the shape memory metal actuator 190 using a strain gauge type resistive heater. Alternately, a small current may be passed directly through the shape memory alloy strip.

Other suitable actuators for use in the transducers described above include rotary drive shafts. FIGS. 14–15 shows one form having a rotary drive shaft 200 which is threaded in four regions 202. The threads in each region differ in pitch. For example, adjacent regions 202 can have thread pitches of 32, 40, 53.3 and 80 threads per inch. As shown in FIG. 14, a support element 204 for a transducer array 206 includes four followers 208, each threadedly engaged with a respective region 202 of the drive shaft 200. When the drive shaft 200 is rotated in an appropriate direction, the varying pitches in the threads of the regions 202 cause the support 204 and therefore the array 206 to be curved convexly as shown in FIG. 15. Generally, the threaded drive shaft 200 may not be fully flexible but may instead have flexible regions interposed between rigid segments. Because of the differential threading in the regions 200, the drive shaft 200 cannot be simply screwed into the followers 208. For this reason it may be preferable for the followers to be assembled to the drive shaft 200 after the drive shaft 200 has been positioned properly with respect to the support element 204.

Another suitable actuator using a rotatable drive shaft is shown in FIG. 16. In this figure the drive shaft 220 includes a thread 222 of steadily increasing pitch. An array 224 is positioned on a support element 226, and the support element 226 includes a follower 228 which in this embodiment is formed of an elastomeric material. The thread 222 can be formed by wrapping a wire around the shaft and securing the wire in place. The shaft 220 can be molded in place in the follower 228 with a suitable mold release agent to prevent adhesion therebetween. By rotating the shaft 200 the follower 228 is compressed, and the array 224 is moved into a convex configuration.

The actuator of FIGS. 17 and 18 includes a rotary drive shaft 240 connected to a curved form 242. The curved form slides within a follower that supports a support element 246 and a transducer array 248. By rotating the drive shaft 240 and the form 242, the array 248 can be caused to assume any one of a wide variety of curvatures.

In the actuators of FIGS. 14–18 a fixed, controlled curvature is obtained by controlling the amount of rotation of the rotary drive shaft 200, 220, 240. A speedometer cable is one construction that can be used for the drive shafts 200, 220, 240, because it has good torsional characteristics. Accuracy can be enhanced further by using a step-down gear system near the array tip so that multiple turns along the long part of the array housing result in a small number of rotations at the array tip, where accuracy is important. Cable rotation can be monitored using a magnetic or optical rotary encoder.

Shape Transducers

The ultrasonic transducers described above use strain gauges as shape transducers to monitor the curvature of the transducer array. Preferably, such strain gauges are selected in terms of material and geometry to provide a high signal level, adequate resistance to design limit strains, and adequate durability over the design life. In some applications it may be preferable to apply strain gauges to both the top and the bottom of the support element so that as one strain gauge contracts the other expands. With this arrangement both strain gauges are coupled to the same side of a Wheatstone bridge so that the voltage potential divider effect is doubled. MicroMeasurements of Raleigh, N.C. manufactures and sells suitable strain gauges to order.

Since the change in the strain-induced resistance in the strain gauge is typically small in this application, it is important to terminate the strain gauge with a high quality electrical conductor or to use a signal conditioning amplifier in the transducer tip. MicroMeasurements sells suitable multistranded cable, typically 26AWG. If necessary shield wire can be used to minimize electromagnetic pickup from the adjacent wires carrying high voltage impulse signals to the PZT elements. An amplifier may be used such as the AD 524 device sold by Analog Devices of Norwood, Mass.

Additionally, a number of measures can be taken to minimize the effects of noise on the low-level signals resulting from the change of resistance in the strain gauges:

1. A low-pass filter can be applied to the output signal of the strain gauge so that only signals less than approximately 10 Hertz are passed. So long as the signals resulting from the maximum rate of flexure change are captured (about one change every second) then all other signals can be regarded as noise and filtered out. This approach minimizes interference from 60 Hertz line signals, transducer pulse repetition rate signals, and transducer signals.

2. As explained above, the sampling of the strain gauge signal in the sampling circuit 24 is preferably synchronized with the transducer pulsing commanded by the transmit beamformer 32 so that the strain gauge signal is sampled during a quiet period of ultrasonic scanning.

In addition to the strain gauges described above, a variety of other shape transducers may be used. For example, semiconductor strain gauges can be used in this application. Semiconductor strain gauges are approximately 10 times more sensitive than conventional resistive strain gauges, but they are substantially more sensitive to temperature fluctuation. This sensitivity makes them less desirable in some applications.

Figure 31:
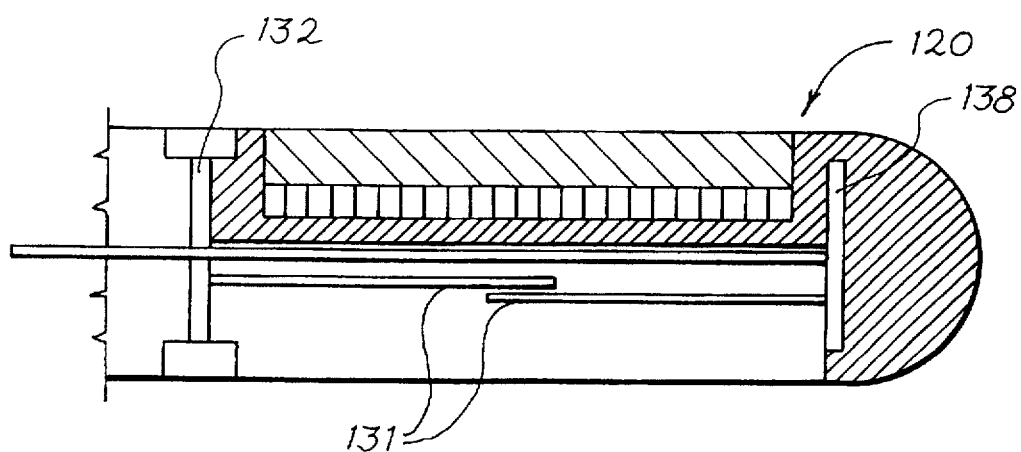
FIG. 31 is a side view of a flexible transducer having a capacitive shape transducer.

Another approach is to use a capacitive sensor as the shape transducer. For example, the transducer 120 of FIG. 4 can include capacitor plates 131 fixed to the anchor plates 132, 138, with a relatively small overlap region, as shown in FIG. 31. These plates 131 are electrically isolated from one another by a thin dielectric sheet. As the array bends the degree of overlap of the plates 131 varies, and therefore the capacitance of the combination varies. Typically, changes in capacitance can be detected as changes in resonant frequency when the capacitor is part of a resonant circuit.

It is not essential in all applications that the shape transducer be carried along with the array of transducer elements or that it directly monitor the shape of a support element for the array. In another approach the shape transducer monitors some portion of the actuator. For example in the embodiment of FIGS. 2–3, a ferromagnetic core can be mounted to the cable 94, and this ferromagnetic core can be arranged to pass through the primary and secondary coils of a coaxial transformer that acts as a linear variable differential transformer. In this way, the position of the cable 94 can be monitored, and the curvature of the array 14 can be inferred. Alternately, a shaft angle encoder can be mounted to the control pulley 100 to achieve the same result.

Since the radius of curvature of the support element is not exactly the same as the radius of curvature of the active surface of the transducer array, and since the position of the actuator similarly does not directly correspond to the radius of curvature of the active surface of the transducer array, it is often preferable to convert the measurements supplied by the shape transducer to a number indicative of the actual curvature of the transducer array. This can be done with a lookup table such as the lookup table 26. Such a lookup table can be embodied as a read only memory that stores a table relating output signal of the shape transducer to actual radius of the transducer array. If there is variability from device to device as a result of manufacturing tolerances, each device can be calibrated at the factory with a calibration table loaded into the read only memory associated with the respective transducer. It should be understood that the curvature may not be constant along the entire length of the transducer array. If the variations in curvature along the length of the array are known, this information can be used by the transmit and receive beamformers and the scan converter to correct for variations in curvature.

Transmit Beamformer

The transmit beamformer 32 generates transmit waveforms that are applied through the multiplexer/demultiplexer 38 to the transducer array 14 (FIG. 1). These transmit waveforms are carefully timed to focus ultrasonic energy in a desired region. Additionally, the amplitudes of the respective transmit waveforms are adjusted in the transmit beamformer 32 to ensure that appropriate energy levels are not exceeded in the tissue being examined, and to provide desired apodizations.

FIGS. 20–22 are schematic diagrams that illustrate the manner in which the delays for the respective transmit waveforms can be determined. FIG. 20 shows the transducer array 14 arranged in a planar configuration. Energy from the array 14 is being focused at the focus F. Straight lines drawn between the focus F and the center of the active surface of respective piezoelectric elements of the array 14 are indicated by the reference number 260. Length differentials of the lines 260 with respect to the shortest line 260 (the central line 260 in this case) are proportional to the time delays appropriate for the transmit waveforms of the respective piezoelectric elements.

As shown in FIG. 21, a similar approach can be used when the array 14 is bent to a convex configuration having a radius R. In this case all delays are calculated without approximation, assuming a straight line propagation path between the center of the respective piezoelectric element and the focus.

As shown in FIG. 22 it may be preferable in some cases to use a two-step approach to determine the required delays in an approximate manner. The first step in this approach is to determine the time delay required for propagation between the focus and a virtual aperture 262, which is rectilinear and positioned in the same position as the active surface of the transducer 14 in FIG. 20. The second step is to determine the time delay for propagation from the center of the active surface of the piezoelectric elements to the respective portions of the virtual aperture 262. These propagation paths are shown at reference numeral 264. Using this approximation method, the total time delay between the focus F and each of the piezoelectric elements of the array 14 is equal to the sum of the delay associated with the respective line 260 and the delay associated with the respective line 264. Note that the projection of the array 14 on the virtual aperture 262 is reduced in length as the array is bent to the convex shape shown in FIG. 22.

Figure 23:
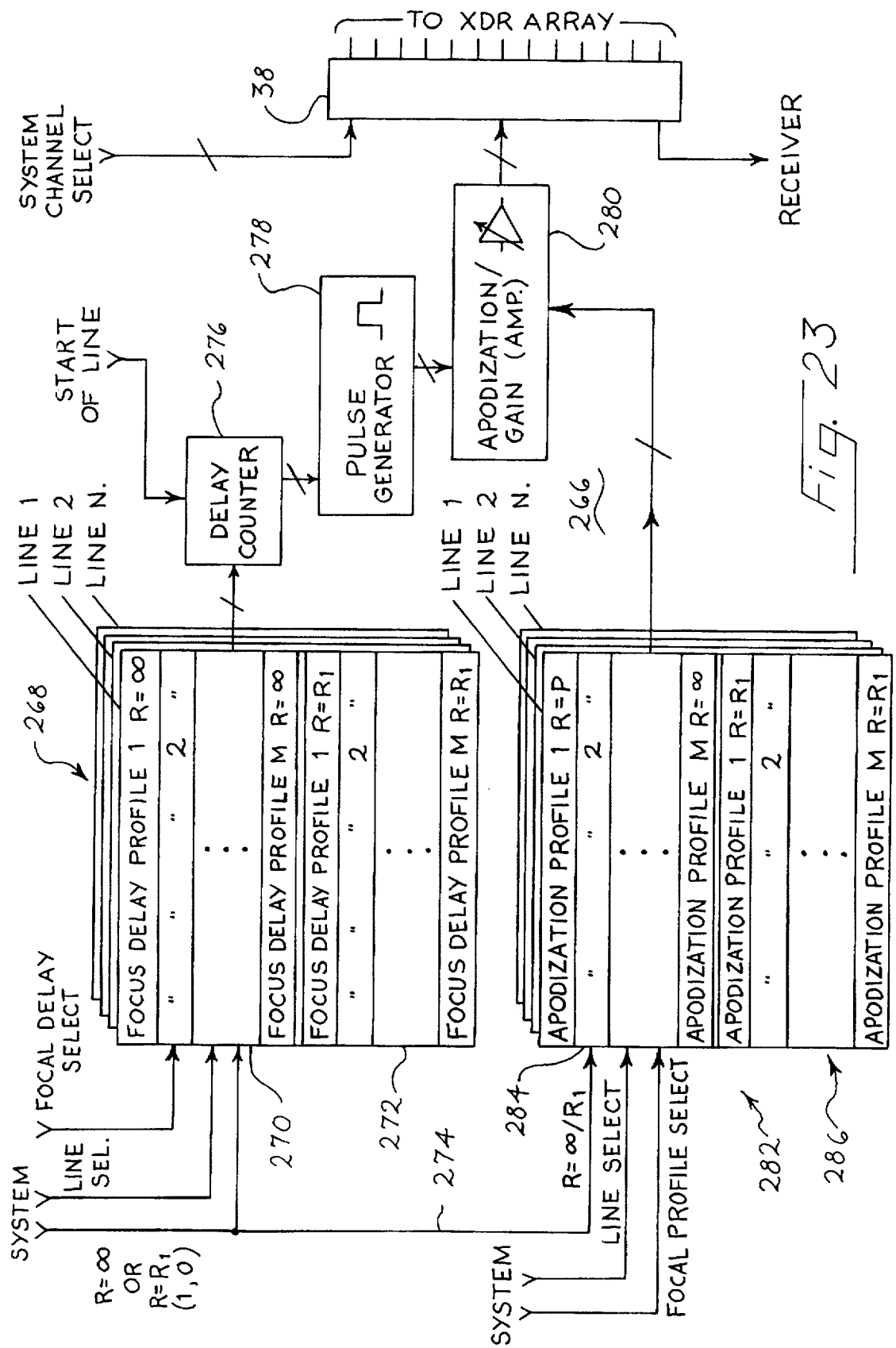
FIG. 23 is a schematic view of transmit beamformer suitable for use in the system of FIG. 1.

FIG. 23 shows a block diagram of a transmit beamformer 266 that operates using the exact method of FIGS. 20 and 21. In the transmit beamformer 262 transmit delays and apodization values are stored for each valid scan format. As a change in curvature of the transducer array is detected, the transmit controller 52 (FIG. 1) commands the transmit beamformer 266 to switch beamforming parameters to the parameters appropriate for the currently prevailing curvature of the transducer array. This is analogous to having a linear array active at one point in time and then disconnecting the linear array and immediately reconnecting a curvilinear array, i.e. switching between arrays plugged into different connectors in the same system.

As shown in FIG. 23, the transmit beamformer 266 includes a delay profile block of memory. This delay profile block 268 stores delay profiles for various focal depths and various scan line numbers. In the simplest case the time delay profiles are constant for all scan lines since the transducer array is a linear array in which lines typically only propagate perpendicularly to the array surface. However, different focusing and/or steering approaches may be used for scan lines at the edge of the frame. For example, by steering the end scan lines a trapezoidal format can be achieved using a linear array.

The delay profile block 268 includes a first section 270 and a second section 272. The section 270 provides time delay profiles for each transducer and each scan line when the transducer array is positioned in the planar position shown in FIG. 20 (i.e. radius=infinity). The second section 272 stores comparable focus delay profiles for each transducer and each scan line number when the transducer is in the configuration shown in FIG. 21 (radius=R1). In this system there are only two valid configurations for the transducer 14, infinity and R1, and the transmit beamformer controller 52 of FIG. 1 identifies on the control line 274 which of these two configurations is currently prevailing.

The selected delays from the delay profile block 268 are (in a simple design configuration) loaded into a delay counter 276, wherein a separate delay counter is used for each transducer channel. After a high level start of line command is received, the counter counts and triggers a pulse generator 278 at the correctly determined time. Lastly, apodization and gain are applied in block 280.

Preferably, apodization values vary as a function of the focal depth and line number, as is well known in conventional systems. Such variation of apodization values is not strictly required, but is preferred for many applications. Furthermore, the beamformer 266 varies the apodization values applied to the apodization/gain block 280 depending upon the curvature of the transducer array. As shown in FIG. 23, the transmit beamformer 266 includes an apodization profile block 282. The block contains two sections 284 and 286. The first section 284 stores apodization values for each transducer element and each scan line, assuming the transducer array is oriented in the flat configuration shown in FIG. 20. The second section 286 stores similar information, assuming the transducer array 14 is curved to the radius R1 as shown in FIG. 21. The apodization profile block 282 is responsive to the control signal on line 274 to select the appropriate apodization profile and to supply this profile to the apodization/gain block 280.

The preferred apodization profile will in many applications vary with the curvature of the transducer array. It may be preferable to change the apodization profile so that, for example, fewer transducer elements are active when the transducer array is moved to a convex shape such as shown in FIG. 21, since fewer transducer elements are pointed along the scan line. For this reason, in many embodiments it will be preferable to replicate the apodization profile block for each valid curvature value of the transducer array.

The output signals from the apodization/gain block 280 are switched to the correct transducer elements of the array 14. The multiplexer/demultiplexer 38 also incorporates conventional protection circuitry so that signal lines applied to the receive beamformer 34 (FIG. 1) are not subject to the relatively high voltages applied to the transducer elements on transmission.

Figure 24:
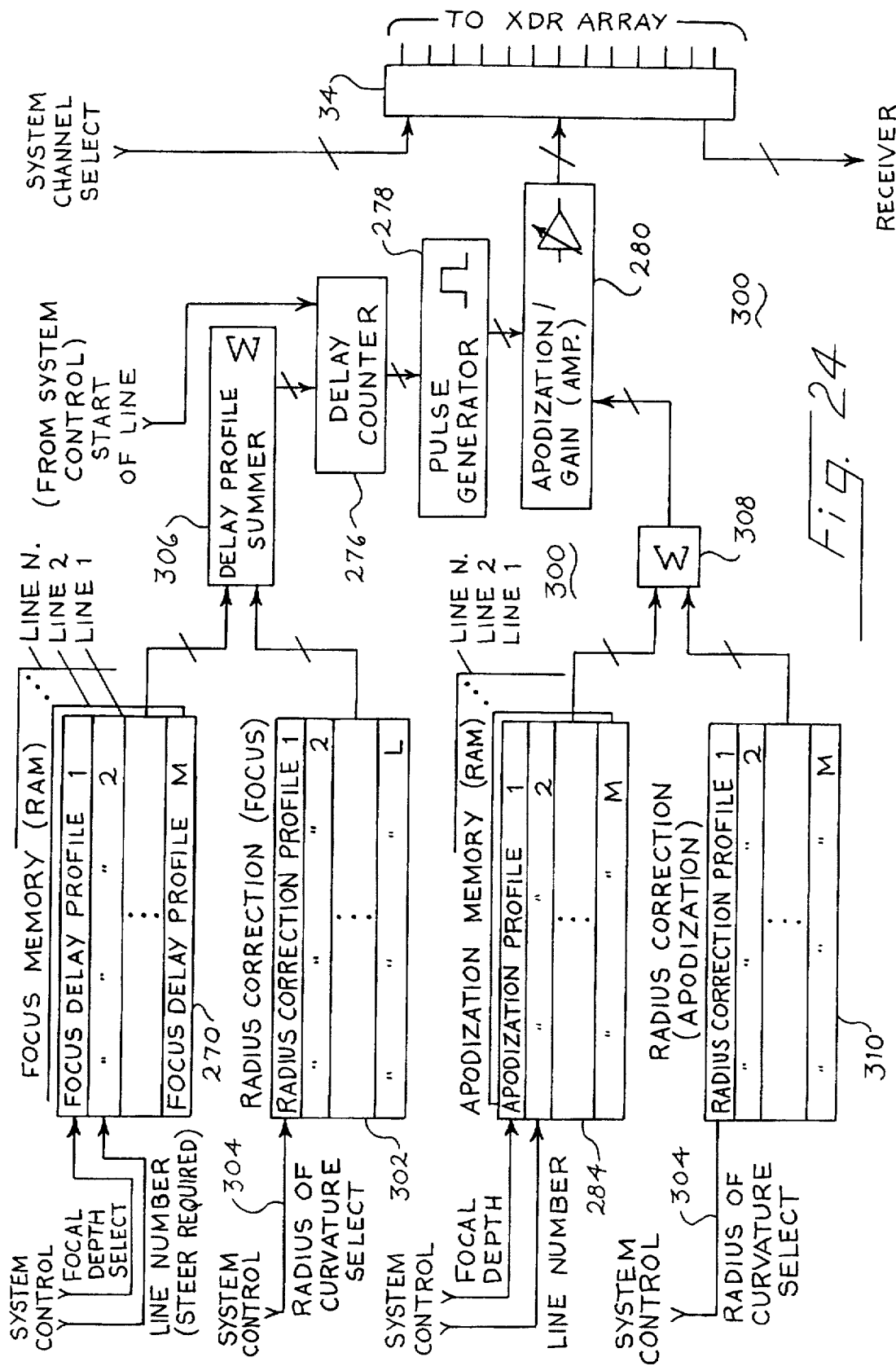
FIG. 24 is a schematic view of an alternative transmit beamformer suitable for use in the system of FIG. 1.

FIG. 24 shows a second transmit beamformer 300, which operates using an approximation method similar to that described above in conjunction with FIG. 22. Comparable components of the beamformers 266, 300 are identified with the same reference numerals.

In the beamformer 300 the first section 270 of the delay profile block and the first section 284 of the apodization profile block are as described above. However in this case correction profiles, which can be either positive or negative, for the transmit delay profiles (calculated on an element-by-element basis) are drawn from a table of precalculated parameters stored in the section 302. In this case the transmit beamformer controller 52 of FIG. 1 generates a radius of curvature select signal on line 304 that selects the correction profile appropriate for the currently prevailing curvature of the transducer array 14 (FIG. 1). The appropriate delays selected from the first section 270 and the section 302 are added together in a summer 306. The output of the summer is applied to the delay counters 276 as described above in conjunction with FIG. 23.

The apodization profile applied to the apodization/gain block 280 is similarly generated by a summer 308. The summer 308 receives a first input from the apodization profile block 284, and a second input from the apodization correction profile block 310. As before, the radius of curvature select signal on line 304 is used to select the appropriate apodization correction profile that corresponds to the instantaneously prevailing curvature of the transducer array.

In some cases the radius of curvature will vary along the length of the array. In such cases, the radius of curvature is also a function of transducer element number or acoustic line number. Typically the radius of curvature will only be detected at a few discrete points along the array. However, it may be assumed that radius of curvature varies in a smooth manner between those known points, and hence intermediate radius of curvature values may be determined by any well known curve-fitting method. Local radius of curvature values are calculated using the curve-fitted values for the origin of all acoustic lines along the array. Therefore, as the system increments acoustic line number as it scans across the array, it also checks the relevant radius of curvature and supplies the nearest available set of curvature correcting delays as held in 302.

Notice that even if there is only one means of detecting radius of curvature, e.g. placed in center, it may be known a priori from design development that the local radii of curvature away from the center are different from the center radius by a determined amount. As an example, as a support is bent, there will be a tendency for the radius of curvature to be tightest near the center due to leverage effects. In this case, the system selects the most suitable correcting delays on a per-line basis using knowledge derived from the radius of curvature detection at the center and the a priori knowledge of the variation of curvature as a function of acoustic line position on the array and detected curvature at the array center.

Figure 25:
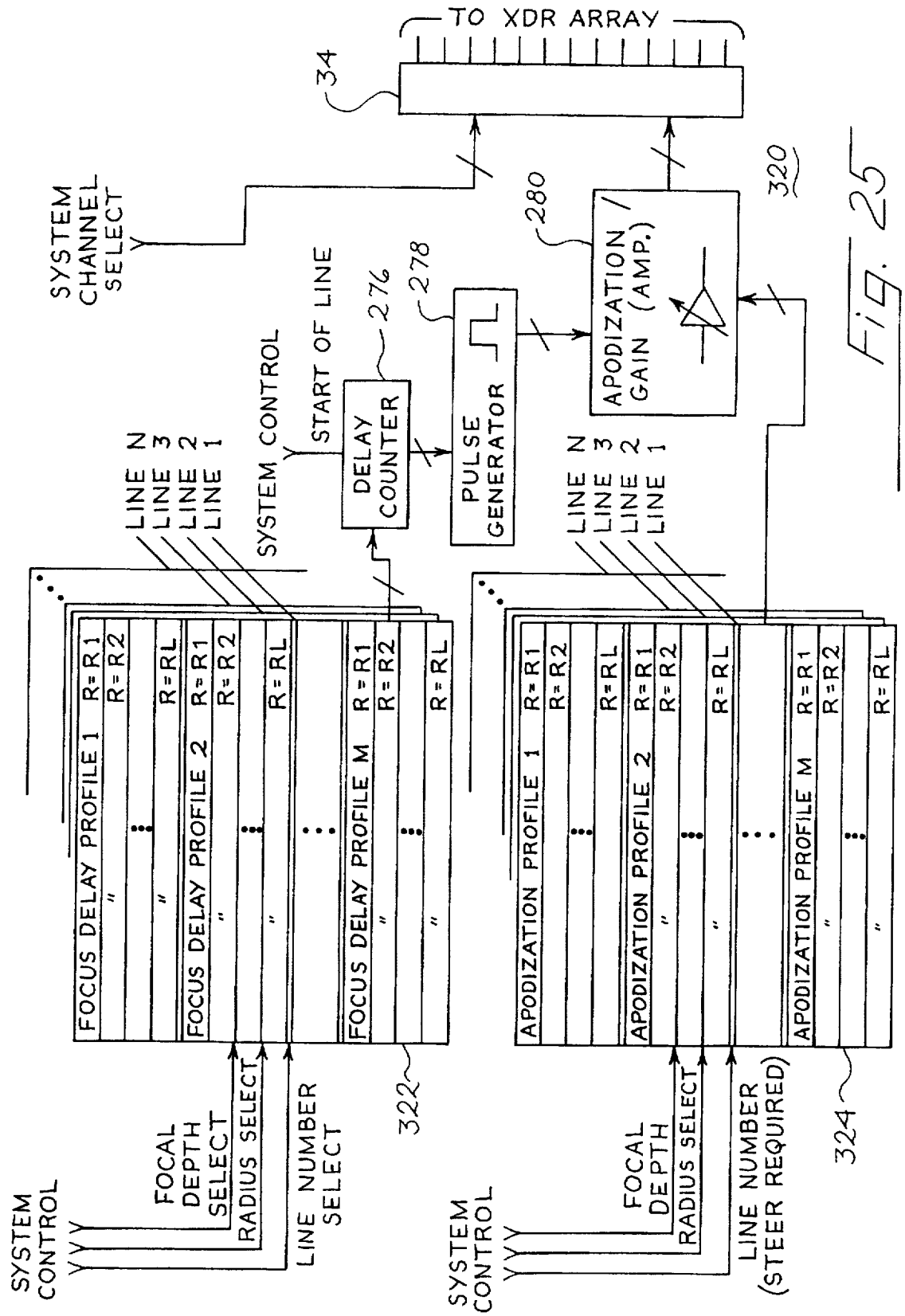
FIG. 25 is a schematic view of a third alterative transmit beamformer suitable for use in the system of FIG. 1.

FIG. 25 shows a third transmit beamformer 320 which operates with a wide range of curvatures of the transducer array, but which does not use the correction approach described above in conjunction with FIGS. 22 and 24. In this case unique focusing profiles are calculated and stored for every focal depth of interest and every valid radius of the transducer array. Additionally, profiles for different scan lines can be stored in the delay profile block 322. Similarly, apodization profiles are calculated and stored in the apodization profile block 324 for every focal depth and every valid radius, and if desired, for every valid scan line. The appropriate profiles are selected from the blocks 322, 324 using a radius select signal generated by the transmit beamformer controller 52 of FIG. 1.

The beamformer 320 uses an approach similar to that of the beamformer 266, but the blocks 322, 324 have been substantially enlarged to accommodate a large number of possible radii for the transducer array. The beamformer 320 requires substantial memory for the blocks 322, 324, but it allows exact calculations of delay since no assumptions are required regarding correction delays as discussed above.

This invention is of course not limited to the specific transmit beamformers discussed above. For example, sophisticated digital transmit beamformers of the type described in U.S. patent application Ser. No. 08/432,056 (assigned to the assignee of the present invention) are believed to be adaptable for use with this invention. Furthermore, the transmit beamformer can operate with all known imaging formats, including B mode imaging, 2-dimensional imaging, color Doppler imaging, pulsed wave and continuous wave Doppler, and the like. Furthermore, the transmit beamformer can include a phase correcting system as described for example in U.S. patent applications Ser. Nos. 8/286,528 and 08/286,664, assigned to the assignee of this invention.

It should be noted that if the neutral axis of the transducer array is behind the active surface of the array, as it will be in many cases, then the individual transducer elements of the array will tend to spread apart slightly as the array is flexed. This effect may be accounted for in the delay compensation calculation. However, since the length of the array shortens as the array is flexed, as discussed above in conjunction with FIG. 22, the effect of element spreading may actually serve to mitigate this problem.

If the array is long and is capable of multiple reversing curves, the local curvature on a line by line case can be calculated by interpolating the local radius of curvature from the position of the scan line origin with respect to the nearest known radius location (i.e. strain gauge location). The number of element-by-element correcting delays may then vary as a function of acoustic line number.

Receive Beamformer

Any of the approaches discussed above in conjunction with transmit beamformers can be applied to the receive beamformer 34.

Figure 26:
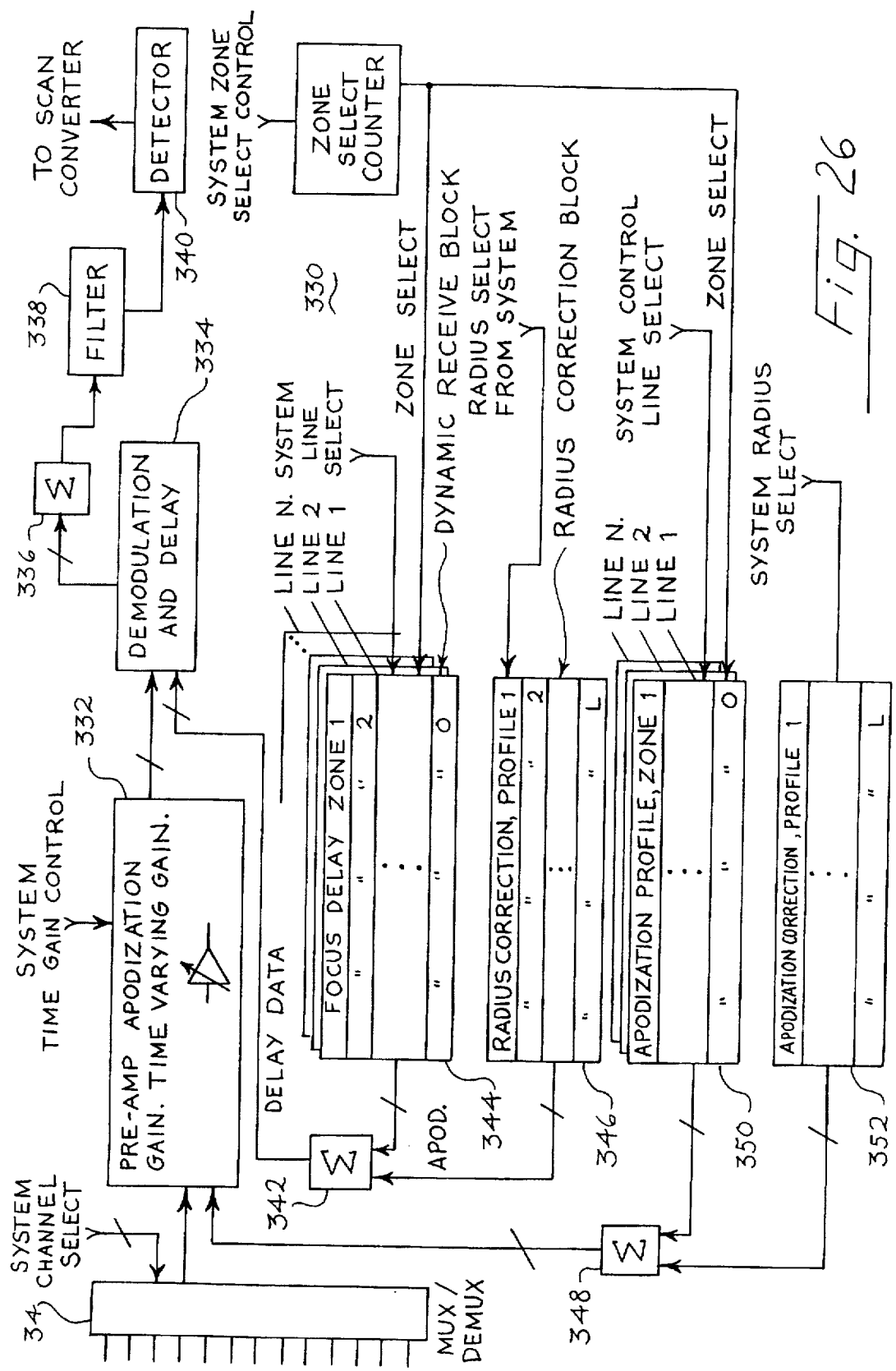
FIG. 26 is a schematic view of a receive beamformer suitable for use in the system of FIG. 1.

FIG. 26 shows a receive beamformer 330 which operates in a manner somewhat similar to the beamformer 300 of FIG. 24. As shown in FIG. 26 receive signals from the transducers of the array 14 are applied by the multiplexer/demultiplexer unit 34 to a preamplifier 332 that provides both apodization gain and time-varying gain on a channel-by-channel basis. The output of the preamplifier 332 is applied to a demodulation and delay block 334. In the block 334 the received signals are demodulated and delayed relative to one another to cause the received signals to add coherently from a selected region of tissue. The output signals of the block 334 are summed in a summer 336, and the output of the summer 336 is applied to a filter 338 and a detector 400. The output of the detector 400 is applied to the scan converter of FIG. 1.

Delay data for the block 334 are provided by a summer 342, that in turn receives signals from a dynamic receive focus delay zone block 404 and a radius correction delay block 346.

The dynamic receive focus delay zone block 344 can be conventional and assumes that the transducer array is flat. Under system control the focus delays applied to the summer 342 from the block 344 are updated on a zone-by-zone basis as a function of time, focusing closely initially and farther out subsequently. It may be more practical to deal with the effect of the radius of the transducer array independently of the dynamic receive updating of focus delay, since it is a high speed hardware operation. Radius correction profiles are calculated for a set of radius values. Appropriate ones of these radius correction profiles are supplied to the adder 342 and are added to the continuously updating dynamic receive focus delays. Ideally, the summation process is pipelined so that summing is performed before the output of the summer is actually required at the input to the delay block 334. In some applications it may be preferable to make the radius correction delays also a function of the scan line number, if a subset of scan lines is being steered.

Similarly, the apodization control signals for the preamplifier 332 are supplied by a summer 348 which receives signals both from an apodization profile block 350 and an apodization correction profile block 352. The receive beamformer controller selects an appropriate one of the apodization profiles for the zone and scan line of interest and applies this profile to the summer 348. Similarly, the receive beamformer controller selects an apodization correction profile appropriate for the instantaneously prevailing radius of the array, and supplies the selected apodization correction profile to the summer 348. In this way the apodization gain for the preamplifier 332 is made to vary as appropriate for the instantaneously prevailing curvature of the transducer array.

Of course, a wide variety of receive beamformers may be adapted for use with this invention, including sophisticated digital receive beamformers of the type described in U.S. patent application Ser. No. 08/432,615 (assigned to the assignee of the present invention).

Scan Converter

The scan converter 36 can operate in much the same manner as conventional scan converters, such as those described by S. Leavitt, et al. in U.S. Pat. Nos. 4,468,747 and 4,471,449, and in the article entitled "A Scan Conversion Algorithm for Displaying Ultrasound Images" (Hewlett-Packard Journal, October, 1983, pp. 30–34). The principal difference is that the scan converter 36 should be adapted to receive updated parameters defining the scan conversion geometry for the instantaneously prevailing curvature of the transducer array on an ongoing basis. Conventional scan converters use such parameters to define the scan geometry of a rigid array having only a single curvature which does not change over time, and it is anticipated that such conventional scan converters can readily be adapted to create the scan converter 36.

Preferably, the scan converter 36 responds to the updated parameters that define the scan conversion geometry for the currently prevailing curvature of the transducer array to create an undistorted image for display. In this way the scan converter adapts the scan conversion geometry as appropriate for the currently prevailing transducer curvature.

Figures 32, 33:
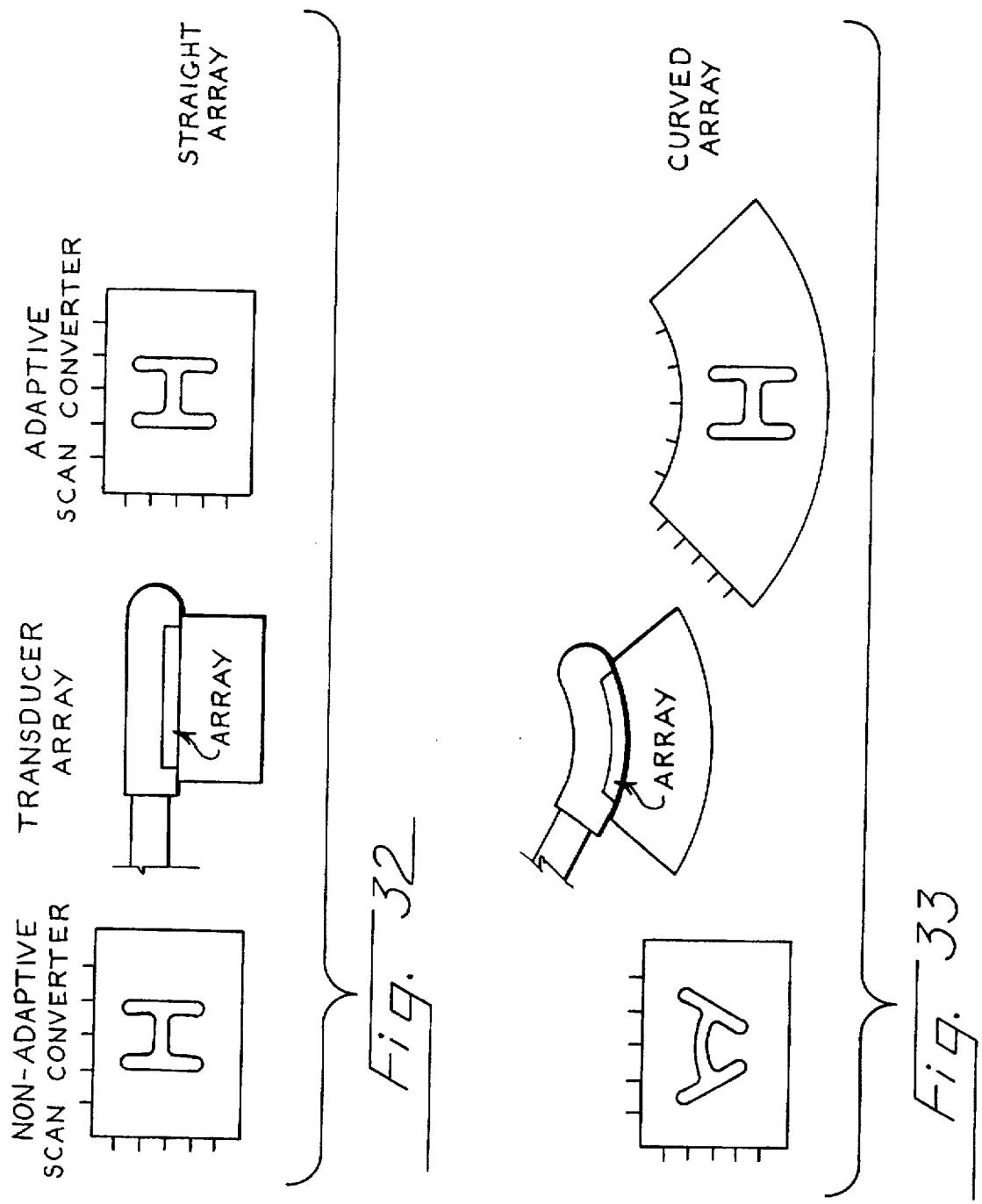
FIGS. 32 and 33 are schematic views comparing images provided by an adapting and a non-adapting scan converter.

FIGS. 32 and 33 illustrate this point. In these figures, images generated by the adaptive scan converter 36 are shown on the right, and images generated by a conventional non-adaptive scan converter are shown on the left. Note that the right hand images remain undistorted, in spite of changes in the shape of the transducer array.

It is anticipated that the scan converter described in Cherry, et al. U.S. patent application Ser. No. 08/433,620, assigned to the assignee of this invention, can be adapted for use as the scan converter 36.

Figure 34:
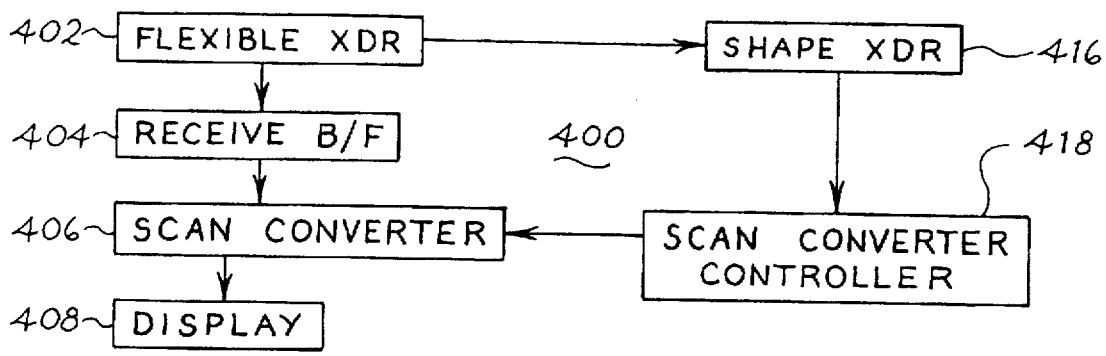
FIG. 34 is a block diagram of an imaging system which incorporates an embodiment of this invention.

FIGS. 34–47 relate to ultrasonic imaging systems in which the scan converter geometry is automatically controlled as appropriate for the instantaneously prevailing curvature of the flexible transducer. As shown in FIG. 34, the imaging system 400 includes a flexible transducer which includes an array of transducer elements that are movable to various curvatures, as described for example in connection with any of the preceding embodiments. The flexible transducer 402 generates transducer receive signals which are applied to a receive beamformer 404, which may also be as described above. The receive beamformer 404 applies appropriate time delays to create beamformed signals, which are applied as inputs to a scan converter 406. Both the receive beamformer 404 and the associated transmit beamformer (not shown) preferably adapt the time delays as appropriate for the instantaneously prevailing curvature of the transducer 402, as discussed in the preceding sections entitled "Transmit Beamformer" and "Receive Beamformer". The scan converter 406 interpolates among the beamformed signals to provide display signals to a display 408. The receive beamformer applies appropriate phase corrections to yield optimal focusing, based on the instantaneously prevailing curvature of the transducer. As explained above, varying curvatures of the transducer 402 result in varying geometries for the beamformed signals generated by the receive beamformer 404.

Figure 35:
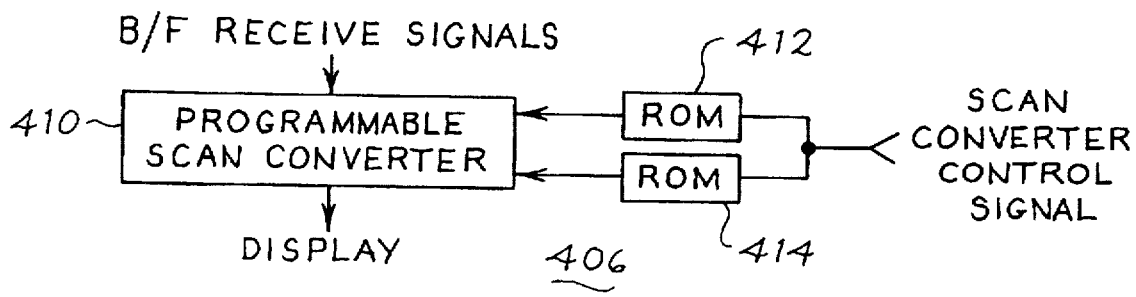
FIG. 35 is a block diagram of the scan converter of FIG. 34.

The scan converter 406 can take the form shown in FIG. 35, including a programmable scan converter 410 that is responsive to one of two sets of programming parameters stored in read only memories 412, 414. The read only memory 412 in this example provides programming parameters appropriate for a scan conversion geometry for a flat transducer array, while the read only memory 414 stores programming parameters appropriate for a scan conversion geometry for a transducer array having a known curvature, for example a constant radius of curvature of 50 millimeters. A scan converter control signal is applied to the read only memories 412 and 414 to program the programmable scan converter 410 to the appropriate geometry.

Figure 47:
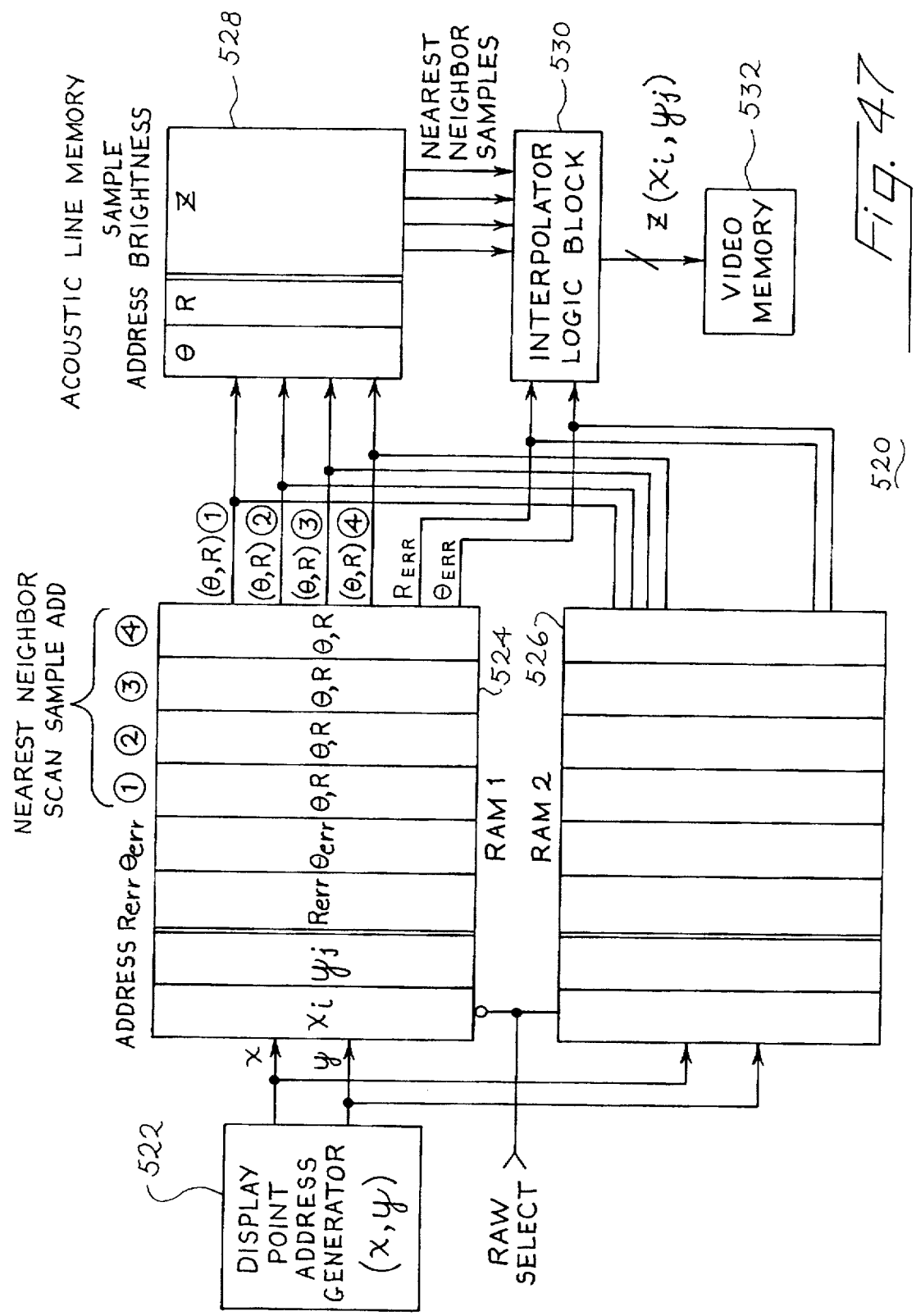
FIG. 47 is a schematic view of another scan converter suitable for use with this invention.

FIGS. 45–47 provide further details regarding suitable scan converters for use in the systems of FIGS. 34–37. FIG. 45 is a schematic representation showing the manner in which acoustic line data is organized along acoustic lines θ at ranges R, where the acoustic lines all meet at an origin (0,0), which is typically off the screen. As an approximation, it may be assumed when the array is flat that the acoustic lines cross at some large but manageable range, such as two meters. This assumption will result in a small error, but it simplifies calculations. The output of the scan converter is organized by X, Y address, suitable for storage in a video memory. As shown in FIG. 45, there is a geometrical relationship between the θ, R coordinates of the acoustic line data and the X, Y coordinates of the video memory. In particular, for point ($X_i$, $Y_j$) the following relationships hold:

$$R=(X_i^2+Y_j^2)^{1/2},$$

$$\theta=\tan^{-1}(X_i/Y_j).$$

FIG. 46 shows a particularly simple scan converter 500. The scan converter 500 includes a display point address generator 502, which generates as an output the X and Y coordinates of a desired pixel. These X and Y coordinates are applied as address inputs to two random access memories 504, 506. The two memories 504, 506 may be substantially identical, except for the stored data. Since the flexible transducer may flex at a relatively high rate, it may be preferable to have two memories as shown, one in active use, and the other being loaded with new data appropriate for a next curvature of the transducer. The two memories 504, 506 are switched by a RAM select signal as appropriate to obtain the desired set of data. As an alternative to the use of two memories which alternate between active and being recalculated or reloaded, a selected number of fixed memories can be used, each of which can be activated when the flexible transducer is in the corresponding configuration.

Each of the memories 504, 506 includes an entry for each possible X, Y address of the video memory, as well as data associated with each address. In this embodiment the data corresponding to each address is simply the θ, R address of the nearest acoustic line data point to the corresponding X, Y address. The determination of which acoustic sample is to be used for each X, Y address is based on a simple geometric calculation made using the curvature of the flexible transducer, since it may be assumed that an acoustic beam emanating from a point along a transducer array is locally normal to the array. For example, if the transducer will assume only two geometries (e.g., flat or radius of curvature equal to 50 millimeters), the θ, R data can be precalculated for these two cases and then stored in the memories 504, 506, respectively.

As shown in FIG. 46, the enabled one of the memories 504, 506 supplies a θ, R address to an acoustic line memory 508. The acoustic line memory 508 stores as data the brightness or Z value for each acoustic line data point, organized by the θ, R address of the acoustic line data. The output of the acoustic line memory 508 is a brightness value Z that is then applied to a video memory 510. The video memory 510 assembles brightness values in the format $Z(X_i, Y_j)$ suitable for display on a video screen. The scan converter 500 avoids interpolation, and for this reason is particularly high speed in operation and inexpensive to implement.

In many applications it is preferable to calculate pixel brightness levels by interpolation. FIG. 47 shows one such scan converter 520. The scan converter 520 uses interpolation techniques described in the paper entitled "A Scan Conversion Algorithm For Displaying Ultrasound Images," by S. C. Levitt, et al. (Hewlett Packard Journal, October 1983, pages 30–34). In particular, the technique described at page 31 of this paper (Equations 1–4) is used. This interpolation technique in effect provides bilinear interpolation along the θ and R axes.

The scan converter 520 includes a display point address generator 522 that supplies an X, Y address to memories 524, 526. As before, one of the two memories 524, 526 is enabled at any one time, as determined by the RAM select signal.

Each of the memories 524, 526 is accessed by an X, Y address, controlled by the display point address generator 522. For each X, Y address, each of the memories 524, 526 provides as output two parameters $R_{ERR}$ and $\theta_{ERR}$, as well as θ, R addresses of the four nearest neighbors. That is, for each X, Y pixel address the nearest four acoustic data points are identified, using the range and θ associated with the X, Y location of interest, and then selecting the four acoustic line data points surrounding this location. The error values $R_{ERR}$ and $\theta_{ERR}$ are defined as in the above-identified article, and they locate the pixel address $X_i, Y_j$ with respect to the four nearest-neighbor acoustic data points.

The θ, R addresses of the four nearest-neighbor acoustic data points are applied from the active one of the two memories 524, 526 to an acoustic line memory 528. The acoustic line memory 528 stores the sample brightness Z for each acoustic line data point at address θ, R. The brightness or Z values for the four selected acoustic line data points are applied by the acoustic line memory 528 to an interpolator logic block 530. This logic block 530 also receives the values $R_{ERR}$ and $\theta_{ERR}$ from the active one of the two memories 524, 526. The interpolator logic block 530 includes hardware or software that provides the interpolation defined by the above-referenced article in order to generate a brightness or Z value $Z(X_i, Y_j)$ for the appropriate pixel. These brightness values are stored in a video memory 532.

Of course, this invention is not limited to use with scan converters as discussed above. Other, more general techniques can be used such that the scan converter can readily be reconfigured as appropriate for any of a wide range of transducer geometries, including transducer geometries having more than two radii of curvature, continuously varying curvatures, and complex recurving shapes. For example, if two neighboring acoustic lines are known for a particular X, Y location, it is only the local curvature relating to that pair of acoustic lines and their location that are needed to define the desired scan conversion geometry for that location.

Returning to FIG. 34, the transducer 402 includes a shape transducer 416 that produces a transducer signal indicative of the instantaneously prevailing curvature of the transducer 402. In this embodiment the transducer signal is applied to a scan converter controller 418, which generates a control signal as a function of the transducer signal, and applies the control signal to the scan converter 406. The transducer signal may vary continuously with curvature of the transducer, and the scan converter controller 418 may convert the transducer signal into a binary signal. For example, the scan converter controller 418 may generate the scan converter control signal at logic level 0 to select the memory 414, 504, 524 when the transducer signal indicates a substantial curvature to the transducer 402, and to a logic level 1 to select the memory 412, 506, 526 when the transducer signal indicates that the transducer 402 has a curvature below a selected level. This approach is well suited for use when the transducer 402 assumes only one of two preselected curvatures, for example as described above in connection with FIGS. 9 and 10.

Figure 36:
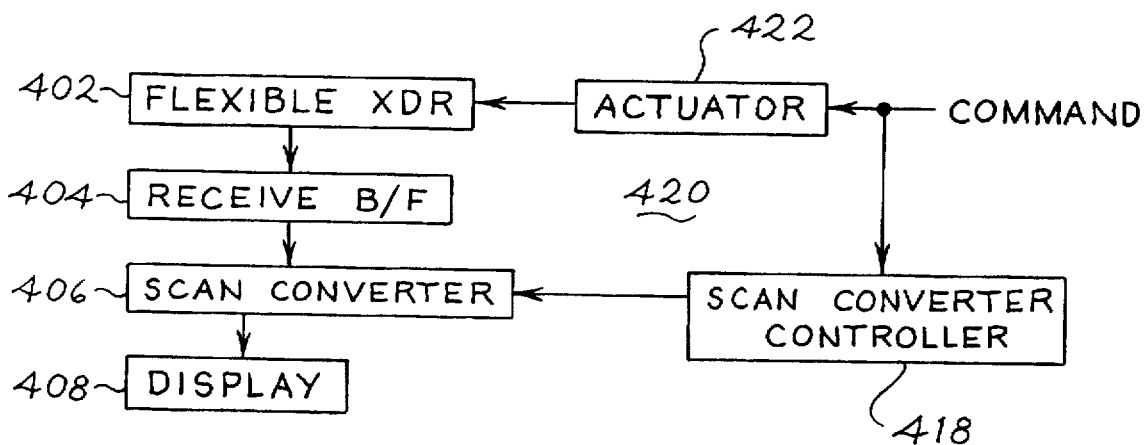
FIG. 36 is a block diagram of another embodiment of the imaging system of this invention.

FIG. 36 shows another ultrasonic imaging system 420 which is similar in many respects to the system 400 of FIG. 34. In FIG. 36 the same reference numerals have been used for comparable elements. In the system 420 the transducer 402 includes an actuator 422 which moves the transducer array of the transducer 402 into one of two selected curvatures in response to a command. The scan converter controller 418 is responsive to this command. As explained above, the command can take many forms. For example, the command may be an electrical signal indicative of the desired curvature of the transducer, or it may be a mechanical signal, such as the position of a control wire for example. In this case the scan converter controller 418 may include a transducer for converting the spatial position of a control wire to an electrical signal suitable for input to the controller 418. As with the system 400 of FIG. 34, the system 420 automatically selects the scan conversion geometry used by the scan converter 406 as appropriate for the instantaneously prevailing curvature of the transducer 402.

Figure 37:
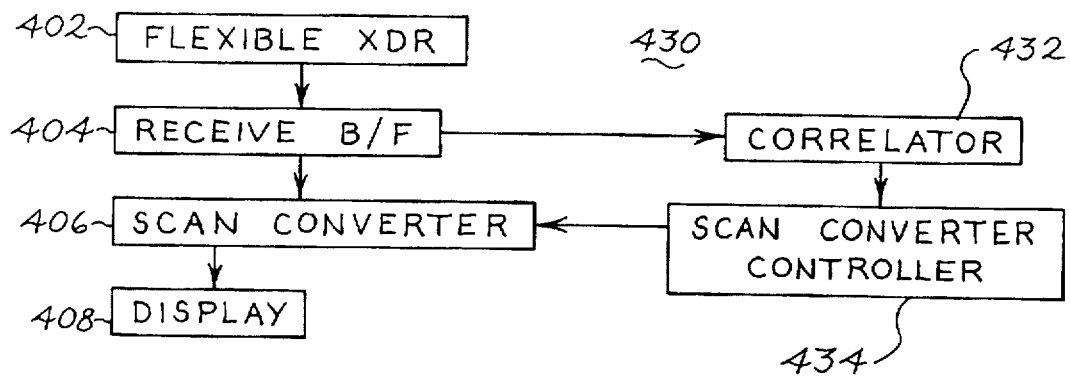
FIG. 37 is a block diagram of yet another embodiment of the imaging system of this invention.

FIG. 37 shows a third ultrasonic imaging system 430 which includes a flexible transducer 402, a receive beamformer 404, a scan converter 406 and a display 408 as described above. The system 430 also includes a correlator 432 which supplies a correlation signal to a scan converter controller 434. These elements are shown in greater detail in the block diagram of FIG. 38.

Figure 38:
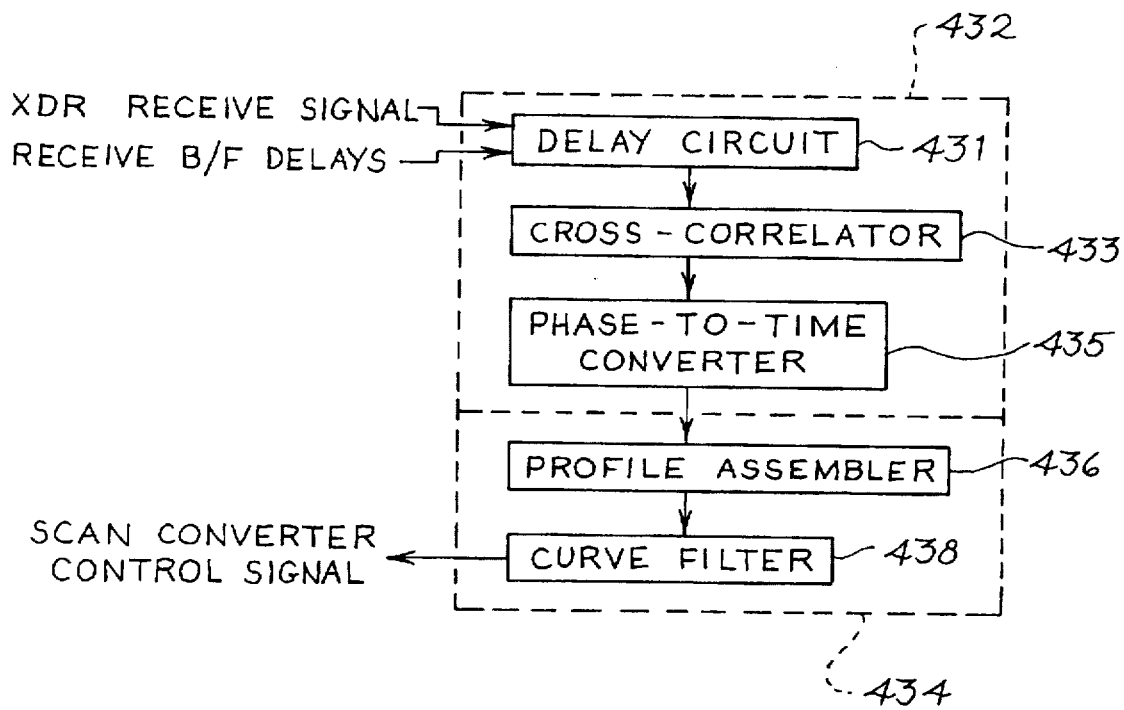
FIG. 38 is a block diagram of the correlator and scan converter controller of FIG. 37.

As shown in FIG. 38, the correlator 432 is responsive to both the transducer receive signals generated by the transducer 402 and to the standard time delays used by the receive beamformer 404 for a flat transducer. Preferably, the transducer receive signals are converted to baseband prior to introduction to the correlator 432. The transducer receive signals are delayed by the standard receive beamformer delays in a delay circuit 431, and the delayed transducer receive signals are applied to a cross-correlator 433. The cross-correlator 433 detects the phase error between the receive signals on adjacent transducer elements and applies these phase errors to a phase-to-time converter 435. The phase-to-time converter 435 converts the phase errors to corresponding time delays, as described for example in U.S. Pat. No. 4,989,143. The converter 435 determines the time delay between the receive signals on adjacent transducer elements, and applies these time delays to the scan converter controller 434.

It should be understood that as used herein, the term "correlator" is intended broadly to encompass any device, whether constructed as a programmed computer or a hardware circuit, that estimates the time of flight differences between the receive signals of adjacent transducer elements. Not all correlators will include cross-correlators as described above. For example, an alternate method suitable for use in a correlator is to measure the time of positive-going zero crossings in the individual transducer receive signals, and to compare these times on adjacent elements to estimate the relative delay. Those skilled in the art will recognize that other techniques can readily be adapted for use with correlators.

The scan converter controller 434 includes a profile assembler 436 that assembles the delays from the correlator 432 into a profile across the active aperture of the transducer 402. A curve fitter 438 then fits a low-order polynomial curve to the profile developed by the profile assembler. The smooth curve provided by the curve fitter 438 may for example be a second order polynomial, fitted using a least squares fit. The curve fitter 438 may include a suitable programmed microcomputer, or it may include a low-pass filtering element. For example, the sequence of detected delays as a function of element number may be processed by simple low-pass filtering, in order to obtain the desired curve. The parameters of this fitted curve are then used to determine the scan converter control signal applied to the scan converter 406 as described above. The delay in time due to the curvature of the array is due to propagation time from the target (to which the system is currently focused) to the particular transducer element displaced from its assumed position in a straight array. Note that for a system which employs a dynamic receive focus (i.e., a receive focus that is continually updated), the delay due to curvature will vary as a function of time since the assumed path geometry is changing. In this case, the delay measurement should be performed at one range and associated time. For the sake of simplicity this should be a farther range rather than a nearer range since the path geometry changes more slowly at this range. Alternatively, the delay measurement may be made at a number of different ranges, taking into account the appropriate path geometry, and the related estimates of element position averaged. Knowing the velocity of sound in tissue, the physical displacement of the transducer array from its position in a straight array can readily be determined. The physical origins of individual acoustic lines along the array are known, and the directions of the acoustic lines are also known, as they are assumed to be locally perpendicular to the plane of the array. In the more general case, the acoustic lines with their origin and direction data are applied to the scan converter, and the scan converter uses the origin and direction data to determine by translation and interpolation the desired pixel values in the normal manner.

Alternately, in the situation where the transducer 402 can assume one of two curvatures (e.g. flat or radius of curvature equal to 50 millimeters), the scan converter controller 434 monitors the parameters determined by the curve fitter 438 to determine whether the instantaneously prevailing curvature of the transducer 402 is closer to 50 millimeters or to a threshold radius of curvature taken as indicative of a flat array. Depending upon this comparison, the scan converter control signal is then set to one of the two binary states discussed above.

Figure 39:
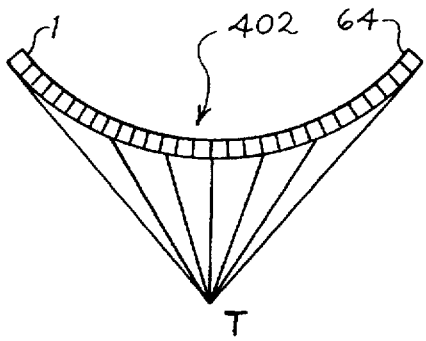
FIG. 39 is a schematic representation of a flexible transducer array.

FIGS. 39-44 illustrate the operation of the correlator 432 and the scan converter controller 434. FIG. 39 shows a schematic view of the transducer array of the transducer 402, including a linear array of transducer elements between element 1 on the extreme left of FIG. 39 and element 64 on the extreme right. As shown in FIG. 39, the array is curved, and is focused at a target T.

The delays among the various transducer receive signals include three different components:

1. The assumed focusing profile for a flat delay in a non-aberating medium. This focusing profile is accounted for in the standard receive beamforming delays. This focusing profile is removed by the block 431 of FIG. 38.

2. A curved profile along the array related to the differential distances caused by the curving of the array. Typically, a smooth curvature over the entire array is associated with curvature of the array. Only certain radii of curvature may be permissible due to the construction of the array.

3. A rapidly varying profile resulting from tissue-related phase aberration. This rapidly varying profile typically has a period of approximately three to five millimeters and is separable from the smoother curved profile of element 2 above.

Figure 40:
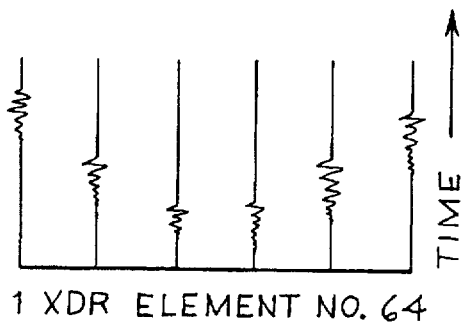
FIG. 40 is a graph showing the output of the delay circuit 431 of FIG. 38.

FIG. 40 shows the transducer receive signals for selected transducer elements between element 1 and element 64, after the beamforming delays appropriate for a flat array have been subtracted in element 431. Note that the receive signals shown in FIG. 40 display a time signature related to the shape of the transducer array of FIG. 39.

Figure 41:
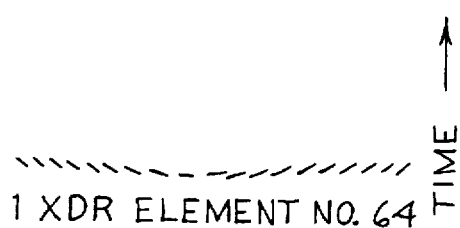
FIG. 41 is a graph showing the output of the phase-to-time converter 435 of FIG. 38.
Figure 42:
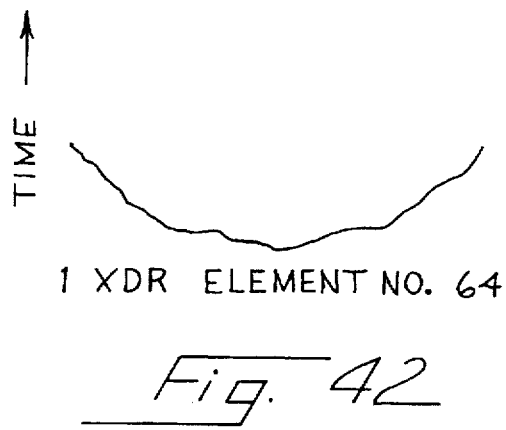
FIG. 42 is a graph showing the output of the profile assembler 436 of FIG. 38.
Figure 43:
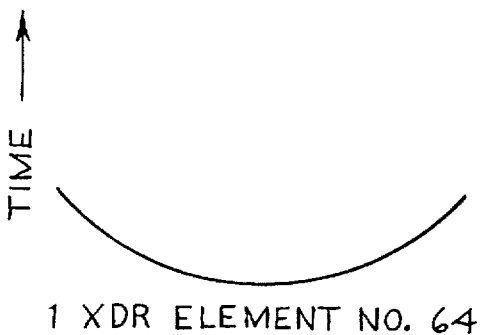
FIG. 43 is a graph showing a smooth curve generated by the curve fitter 438 of FIG. 38.
Figure 44:
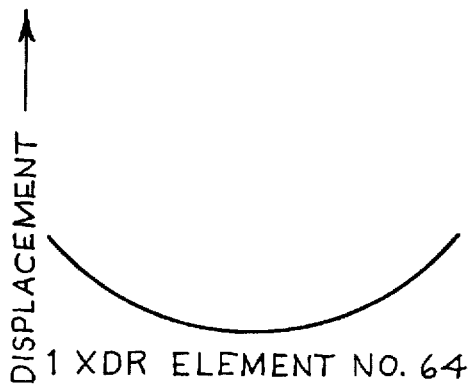
FIG. 44 is a graph showing the calculated displacement of the transducer 402 of FIG. 39, as determined by the curve fitter 438 of FIG. 38.

As shown in FIG. 41, the cross-correlator 433 and the phase-to-time converter 435 determine the delays between the transducer receive signals for adjacent transducer elements. FIG. 42 shows the profile assembled in the profile assembler 436 from the individual delays. Note that there are small high frequency variations in the profile of FIG. 42 due to tissue inhomogeneity, along with an overall curvature related to the curvature of the transducer array. FIG. 43 shows a smooth curve fitted to the profile of FIG. 42, and FIG. 44 shows the corresponding curve in units of transducer displacement. These curves eliminate the high frequency variation due to tissue inhomogeneity, and the curve of FIG. 44 exhibits curve fit parameters indicative of the instantaneously prevailing curvature of the transducer array. In this way, the curvature of the transducer array is inferred from the pattern of delays actually observed with the transducer array.

Once the smooth curve of FIG. 43 has been determined, this smooth curve may be subtracted from the curve of FIG. 42 to determine the high frequency phase variations due to tissue inhomogeneity. These high frequency phase variations can then be used to improve the focus of the transmit and receive beamformers. See, e.g., the discussion in U.S. Pat. No. 5,551,433 of prior art adaptive focus systems.

The above-referenced article by Pai-Chi Li and Matthew O'Donnell ("Phase Aberration Correction on Two-Dimensional Conformal Arrays", IEEE Transactions on Ultrasonics, Ferroelectrics, and Frequency Control, Vol. 42, No. 1, January 1995, pp. 73-82) should be referenced for a detailed explanation of the manner in which cross-correlation techniques can be used to derive phase profiles, and the manner in which low order (array curvature) and higher order (tissue aberration) delays can be extracted from the phase profile. The measurement of curvature of the transducer may be made across all of the transducer array, or only portions of the array. Typically, the mechanical design of the transducer will only permit a certain range of curvatures along the array, and this information can be used to check the validity of the estimated curvature. For example, it may be known that the array will bend (due to differing moments along the array) with a radius of 50 millimeters in the middle of the array, with a radius of 60 millimeters at the ends of the array, and with a smoothly varying local radius at points between the middle and ends of the array.

The methods described above for estimating the curvature of the array based on cross-correlation techniques may be made iterative as described in U.S. Pat. No. 4,989,143. In this case previous estimates of curvature and phase aberating profile are used as an input for successively applied delays and phase difference measurements. Such iterative methods are expected to provide improved results.

Optionally, the curvature as detected by the correlator can be used to update the delay profiles used by the transmit and receive beamformers. In this case, account must be taken of these updated delay profiles when calculating the new array curvature, since the delays measured consist of those due to the geometric path length minus the delays applied due to the assumed curvature programmed in the beamformer. Once a new measure of curvature has been derived, this is added to the old curvature as applied to the beamformer in the current beam firing and used in subsequent beam firings. Note that by making the beamformers adapt to the current curvature a more coherent target echo will be generated and hence measurements of delay will be more accurate.

As used herein, a signal is considered to be supplied by one element to another whether it is supplied directly (without intervening processing) or indirectly (via intervening processing). Similarly, an element is considered to be responsive to another element whether it is responsive directly (without intervening elements) or indirectly (via intervening elements). Similarly, two elements are said to be coupled to one another whether they are coupled directly or indirectly via intermediate elements.

Conclusion

From the foregoing, it should be apparent that the present invention can be implemented in many ways, using a wide variety of transducers, actuators, shape transducers, beamformers, displays and warning devices. It should be understood that the foregoing detailed description is intended by way of illustration only. It is the following claims, including all equivalents, which are intended to define the scope of this invention.

I claim:

1. In an ultrasonic imaging system of the type comprising a receive beamformer, the improvement comprising:

an ultrasonic transducer comprising a plurality of ultrasonic transducer elements, said transducer elements movable between at least first and second configurations which differ in curvature, said transducer elements supplying receive signals to the receive beamformer;

a scan converter controller operative to generate a control signal indicative of configuration of the transducer elements;

a scan converter, said scan converter responsive to the receive beamformer and to the control signal to reduce image distortion associated with movement of the transducer elements between the first and second configurations.

2. The invention of claim 1 wherein the transducer comprises a shape transducer operative to generate a transducer signal indicative of configuration of the transducer elements, and wherein the scan converter controller is responsive to the transducer signal.

3. The invention of claim 1 wherein the transducer comprises an actuator coupled to the transducer elements to move the transducer elements between the first and second configurations in response to an actuator command, and wherein the scan converter controller is responsive to the actuator command.

4. The invention of claim 1 wherein the scan converter controller comprises a correlator responsive to the receive signals to estimate configuration of the transducer elements.

5. In an ultrasonic imaging system of the type comprising a flexible ultrasonic transducer which generates a plurality of transducer receive signals, and a receive beamformer receive to the transducer receive signals to generate a plurality of beamformed receive signals, the improvement comprising:

means for monitoring a curvature of the flexible transducer; and means for scan converting the beamformed receive signals using a scan conversion geometry selected in response to the curvature of the flexible transducer as monitored by the monitoring means.

6. The invention of claim 5 wherein the transducer comprises a shape transducer operative to generate a transducer signal indicative of curvature of the transducer, and wherein the monitoring means is responsive to the transducer signal.

7. The invention of claim 5 wherein the transducer comprises an actuator operative to alter curvature of the transducer in response to an actuator command, and wherein the monitoring means is responsive to the actuator command.

8. The invention of claim 5 wherein the monitoring means comprises a correlator responsive to the transducer receive signals to estimate the curvature of the transducer.

9. A method for displaying ultrasonic images with an imaging system comprising a flexible ultrasonic transducer and a receive beamformer responsive to the transducer to generate a plurality of beamformed receive signals, said method comprising the following steps:

(a) monitoring a curvature of the flexible transducer; and (b) scan converting the beamformed receive signals using a scan conversion geometry selected in response to the curvature of the flexible transducer monitored in step (a).

10. The method of claim 9 wherein the transducer comprises a shape transducer operative to generate a transducer signal indicative of curvature of the transducer, and wherein step (a) comprises the step of monitoring the transducer signal.

11. The method of claim 9 wherein the transducer comprises an actuator operative to alter curvature of the transducer in response to an actuator command, and wherein step (a) comprises the step of monitoring the actuator command.

12. The method of claim 9 wherein step (a) comprises the step of correlating transducer receive signals generated by the transducer to estimate the curvature of the transducer.

13. The method of claim 9 further comprising the step of (c) using the curvature monitored in step (a) to update a beamformer delay profile.

14. The method of claim 13 wherein the beamformer delay profile is used by the receive beamformer.

* * * * *

UNITED STATES PATENT AND TRADEMARK OFFICE
CERTIFICATE OF CORRECTION

PATENT NO. : 5,735,282
DATED : April 7, 1998
INVENTOR(S) : John A. Hossack

It is certified that error appears in the above-identified patent and that said Letters Patent is hereby corrected as shown below:

In column 6, line 41, after "this" insert --is--.

In column 6, line 54, replace "numbers" with --members--.

In column 6, line 60, delete "as" (second occurrence).

In column 7, line 20, replace "a" with --as--.

In column 10, line 65, replace "shows" with --show--.

In the Claims

In Claim 13, line 2, replace "(c)" with --(b)--.

Signed and Sealed this

Fourteenth Day of September, 1999

Attest:

Q. TODD DICKINSON

*Attesting Officer*   *Acting Commissioner of Patents and Trademarks*